(12) United States Patent
Mansbridge

(10) Patent No.: US 7,160,726 B2
(45) Date of Patent: *Jan. 9, 2007

(54) COMPOSITIONS COMPRISING CONDITIONED CELL CULTURE MEDIA AND USES THEREOF

(75) Inventor: Jonathan N. Mansbridge, La Jolla, CA (US)

(73) Assignee: Skin Medica, Inc., Carlsbad, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/165,860

(22) Filed: Jun. 7, 2002

(65) Prior Publication Data

US 2004/0142861 A1 Jul. 22, 2004

Related U.S. Application Data

(60) Provisional application No. 60/297,177, filed on Jun. 7, 2001.

(51) Int. Cl.
*C12N 5/00* (2006.01)
*C12N 5/08* (2006.01)

(52) U.S. Cl. ............... 435/391; 435/325; 435/366; 435/371; 435/395; 424/198.1; 514/2

(58) Field of Classification Search ............ None
See application file for complete search history.

(56) References Cited

U.S. PATENT DOCUMENTS

| | | | |
|---|---|---|---|
| 5,091,173 A * | 2/1992 | Buultjens et al. ............ 514/3 |
| 5,229,493 A | 7/1993 | Folkman et al. ........... 530/350 |
| 5,888,551 A * | 3/1999 | Jimenez et al. ............ 424/534 |
| 5,935,849 A | 8/1999 | Schinstine et al. ......... 435/325 |
| 5,965,125 A | 10/1999 | Mineau-Hanschke ...... 424/93.21 |
| 6,372,494 B1 * | 4/2002 | Naughton et al. .......... 435/391 |

FOREIGN PATENT DOCUMENTS

| | | |
|---|---|---|
| WO | WO 93 04164 | 3/1993 |
| WO | WO 96 18726 | 6/1996 |
| WO | WO 97 21442 | 6/1997 |
| WO | WO 98/21312 | 11/1997 |
| WO | WO 00 46349 | 8/2000 |

OTHER PUBLICATIONS

Pinney, Emmett et al., "Human Three-Dimensional Fibroblast Cultures Express Angionenic Activity," Journal of Cellular Physiology, vol. 183, No. 1, Apr. 2000, pp. 74-82.
Pinney, Emmett et al., "Wound Healing Potential of Dermagraft® Conditioned Medium," Journal of Investigative Dermatology, vol. 114, No. 4, Apr. 2000, p. 828.

* cited by examiner

*Primary Examiner*—Eileen B. O'Hara
(74) *Attorney, Agent, or Firm*—Wilson Sonsini Goodrich & Rosati

(57) ABSTRACT

The invention relates to compositions comprising cell culture medium conditioned by cells grown in three-dimensional culture. The cells used to condition the medium may be genetically modified to alter the concentration of growth factors and antioxidants in the medium. The conditioned cell medium (conditioned medium) may be used for at least one of cosmetic applications, cosmeceutical applications, and pharmaceutical applications, among other things. The invention also relates to proteins comprising a heterologous sequence that enhances cell penetration. The invention also relates to cells comprising DNA encoding such proteins. Methods for preparing the inventive compounds are also provided.

48 Claims, 6 Drawing Sheets

SEQUENCE LISTING

<160> NUMBER OF SEQ ID NOS: 24

<210> SEQ ID NO 1
<211> LENGTH: 16
<212> TYPE: PRT
<213> ORGANISM: Drosophila melanogaster

<400> SEQUENCE: 1

Arg Gln Ile Lys Ile Trp Phe Gln Asn Arg Arg Met Lys Trp Lys Lys
1               5                   10                  15

<210> SEQ ID NO 2
<211> LENGTH: 16
<212> TYPE: PRT
<213> ORGANISM: Drosophila melanogaster

<400> SEQUENCE: 2

Arg Gln Ile Lys Ile Trp Phe Pro Asn Arg Arg Met Lys Trp Lys Lys
1               5                   10                  15

<210> SEQ ID NO 3
<211> LENGTH: 9
<212> TYPE: PRT
<213> ORGANISM: Human immunodeficiency virus type 1

<400> SEQUENCE: 3

Arg Lys Lys Arg Arg Gln Arg Arg Arg
1               5

```
<210> SEQ ID NO 4
<211> LENGTH: 27
<212> TYPE: PRT
<213> ORGANISM: Artificial
<220> FEATURE:
<223> OTHER INFORMATION: derived from galanin and mastoparan

<400> SEQUENCE: 4

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 5
<211> LENGTH: 17
<212> TYPE: PRT
<213> ORGANISM: Human immunodeficiency virus type 1

<400> SEQUENCE: 5

Thr Arg Gln Ala Arg Arg Asn Arg Arg Arg Arg Trp Arg Glu Arg Gln
1               5                   10                  15

Arg

<210> SEQ ID NO 6
<211> LENGTH: 15
<212> TYPE: PRT
<213> ORGANISM: Human immunodeficiency virus type 1

<400> SEQUENCE: 6

Arg Arg Arg Arg Asn Arg Thr Arg Arg Asn Arg Arg Arg Val Arg
1               5                   10                  15

<210> SEQ ID NO 7
<211> LENGTH: 19
<212> TYPE: PRT
<213> ORGANISM: Brome mosaic virus

<400> SEQUENCE: 7

Lys Met Thr Arg Ala Gln Arg Arg Ala Ala Ala Arg Arg Asn Arg Trp
1               5                   10                  15

Thr Ala Arg

<210> SEQ ID NO 8
<211> LENGTH: 13
<212> TYPE: PRT
<213> ORGANISM: Human immunodeficiency virus type 2

<400> SEQUENCE: 8

Thr Arg Arg Gln Arg Thr Arg Arg Ala Arg Arg Asn Arg
1               5                   10

<210> SEQ ID NO 9
<211> LENGTH: 19
<212> TYPE: PRT
<213> ORGANISM: Cowpea chlorotic mottle virus

<400> SEQUENCE: 9

Lys Leu Thr Arg Ala Gln Arg Arg Ala Ala Ala Arg Lys Asn Lys Arg
1               5                   10                  15

Asn Thr Arg

<210> SEQ ID NO 10
```

```
<211> LENGTH: 17
<212> TYPE: PRT
<213> ORGANISM: Bacteriophage lambda

<400> SEQUENCE: 10

Asn Ala Lys Thr Arg Arg His Glu Arg Arg Arg Lys Leu Ala Ile Glu
1               5                   10                  15

Arg

<210> SEQ ID NO 11
<211> LENGTH: 22
<212> TYPE: PRT
<213> ORGANISM: Bacteriophage lambda

<400> SEQUENCE: 11

Met Asp Ala Gln Thr Arg Arg Arg Glu Arg Arg Ala Glu Lys Gln Ala
1               5                   10                  15

Gln Trp Lys Ala Ala Asn
            20

<210> SEQ ID NO 12
<211> LENGTH: 18
<212> TYPE: PRT
<213> ORGANISM: Bacteriophage phi-21

<400> SEQUENCE: 12

Thr Ala Lys Thr Arg Tyr Lys Ala Arg Arg Ala Glu Leu Ile Ala Glu
1               5                   10                  15

Arg Arg

<210> SEQ ID NO 13
<211> LENGTH: 16
<212> TYPE: PRT
<213> ORGANISM: Saccharomyces cerevisiae

<400> SEQUENCE: 13

Thr Arg Arg Asn Lys Arg Asn Arg Lys Gln Glu Gln Leu Asn Leu Lys
1               5                   10                  15

<210> SEQ ID NO 14
<211> LENGTH: 26
<212> TYPE: PRT
<213> ORGANISM: Homo sapiens

<400> SEQUENCE: 14

Lys Arg Arg Ile Arg Arg Glu Arg Gln Lys Met Ala Ala Ala Lys Ser
1               5                   10                  15

Arg Asn Arg Arg Arg Glu Leu Thr Asp Thr
            20                  25

<210> SEQ ID NO 15
<211> LENGTH: 13
<212> TYPE: PRT
<213> ORGANISM: Human immunodeficiency virus type 1

<400> SEQUENCE: 15

Gly Arg Lys Lys Arg Arg Gln Arg Arg Arg Pro Pro Gln
1               5                   10

<210> SEQ ID NO 16
<211> LENGTH: 13
<212> TYPE: PRT
<213> ORGANISM: Human immunodeficiency virus type 1
```

```
<400> SEQUENCE: 16

Gly Arg Arg Arg Arg Arg Arg Arg Pro Pro Gln
1               5                   10

<210> SEQ ID NO 17
<211> LENGTH: 28
<212> TYPE: PRT
<213> ORGANISM: Homo sapiens

<400> SEQUENCE: 17

Arg Ile Lys Ala Glu Arg Lys Arg Met Arg Asn Arg Ile Ala Ala Ser
1               5                   10                  15

Lys Ser Arg Lys Arg Lys Leu Glu Arg Ile Ala Arg
            20                  25

<210> SEQ ID NO 18
<211> LENGTH: 6
<212> TYPE: PRT
<213> ORGANISM: Artificial
<220> FEATURE:
<223> OTHER INFORMATION: completely synthesized

<400> SEQUENCE: 18

Arg Arg Arg Arg Arg Arg
1               5

<210> SEQ ID NO 19
<211> LENGTH: 22
<212> TYPE: PRT
<213> ORGANISM: Saccharomyces cerevisiae

<400> SEQUENCE: 19

Lys Arg Ala Arg Asn Thr Glu Ala Ala Arg Arg Ser Arg Ala Arg Lys
1               5                   10                  15

Leu Gln Arg Met Lys Gln
            20

<210> SEQ ID NO 20
<211> LENGTH: 27
<212> TYPE: RNA
<213> ORGANISM: Artificial
<220> FEATURE:
<223> OTHER INFORMATION: exemplary sequence encoding SEQ ID NO:3

<400> SEQUENCE: 20
cguaaaaaac gucgucaacg ucgucgu                                              27

<210> SEQ ID NO 21
<211> LENGTH: 27
<212> TYPE: RNA
<213> ORGANISM: Artificial
<220> FEATURE:
<223> OTHER INFORMATION: exemplary sequence encoding SEQ ID NO:3

<400> SEQUENCE: 21
cgcaaaaaac gccgccaacg ccgccgc                                              27

<210> SEQ ID NO 22
<211> LENGTH: 18
<212> TYPE: RNA
<213> ORGANISM: Artificial
<220> FEATURE:
<223> OTHER INFORMATION: exemplary sequence encoding SEQ ID NO:18
```

```
<400> SEQUENCE: 22
agaagaagaa gaagaaga                                                    18

<210> SEQ ID NO 23
<211> LENGTH: 9
<212> TYPE: RNA
<213> ORGANISM: Artificial
<220> FEATURE:
<223> OTHER INFORMATION: exemplary sequence encoding glutathione
                        (gamma-glutamylcysteinylglycine)

<400> SEQUENCE: 23 caauguggu                                                               9

<210> SEQ ID NO 24
<211> LENGTH: 9
<212> TYPE: RNA
<213> ORGANISM: Artificial
<220> FEATURE:
<223> OTHER INFORMATION: exemplary sequence encoding glutathione
                        (gamma-glutamylcysteinylglycine)

<400> SEQUENCE: 24 cauguggc                                                                9
```

COMPOSITIONS COMPRISING CONDITIONED CELL CULTURE MEDIA AND USES THEREOF

RELATED APPLICATIONS

This application claims priority of provisional U.S. Patent Application Ser. No. 60/297,177, filed Jun. 7, 2001, which is expressly incorporated herein by reference, in its entirety, for any purpose. This application is related to U.S. patent application Ser. No.: 09/313,538, filed May 14, 1999, which is expressly incorporated herein by reference, in its entirety, for any purpose.

FIELD OF THE INVENTION

The invention relates to compositions comprising cell culture medium conditioned by cells grown in three-dimensional culture. The cells used to condition the medium may be genetically modified to alter the concentration of growth factors and antioxidants in the medium. The conditioned cell medium (conditioned medium) is useful in cosmetic applications, cosmeceutical applications, and pharmaceutical applications, among other things. The invention also includes proteins comprising a peptide sequence that enhances cell penetration, DNA encoding such proteins, and cells containing such DNA. Methods for preparing the inventive compounds are also provided.

SUMMARY OF THE INVENTION

The present invention is directed to compositions comprising conditioned cell culture medium, or an extract thereof, generated using three-dimensional cell cultures and an appropriate carrier. The invention is also directed to methods for preparing such compositions. In certain embodiments, the three-dimensional culture comprises eukaryotic cells or human cells, particularly dermal fibroblasts, keratinocytes, epithelial cells, chondrocytes, smooth muscle cells, and myocytes. In certain embodiments the appropriate carrier is a pharmaceutically-acceptable carrier, a cosmetically-acceptable carrier, or a cosmeceutically-acceptable carrier. In certain embodiments, the conditioned cell culture media is generated using pre-conditioned media that is serum-free or animal product-free.

In certain embodiments, the conditioned media comprises at least one genetically-engineered growth factor or at least one genetically-engineered antioxidant. In certain embodiments, the compositions of the invention comprise at least one genetically-engineered growth factor, at least one genetically-engineered antioxidant, at least one genetically-engineered extracellular matrix component, or combinations thereof. In certain embodiments, the at least one genetically-engineered growth factor, the at least one genetically-engineered antioxidant, or the at least one genetically-engineered extracellular matrix component comprises at least one transport-enhanced growth factor, transport-enhanced antioxidant, or transport-enhanced extracellular matrix component. In certain embodiments, the transport-enhanced growth factor, transport-enhanced antioxidant, or transport-enhanced extracellular matrix component further comprises one of the amino acid sequences of Table 1 (SEQ ID NO:1–SEQ ID NO: 19).

In certain embodiments, a growth factor comprising a heterologous peptide sequence that enhances cell penetration is provided. In certain embodiments a cell comprising DNA encoding a growth factor comprising a heterologous peptide sequence that enhances cell penetration is provided.

In certain embodiments an antioxidant comprising a heterologous peptide sequence that enhances cell penetration is provided. In certain embodiments a cell comprising DNA encoding an antioxidant comprising a heterologous peptide sequence that enhances cell penetration is provided.

In certain embodiments an extracellular matrix component comprising a heterologous peptide sequence that enhances cell penetration is provided. In certain embodiments a cell comprising DNA encoding an extracellular matrix component comprising a heterologous peptide sequence that enhances cell penetration is provided.

In certain embodiments, the inventive compositions comprise lotions, creams, gels, including hydrogels, powders, serums, salves, foundations, facial masks, lip care products, sunscreens, hair care products, such as shampoos, conditioners, including deep conditioners, hair care treatments, hot oil treatments, and the like, skin cleansers, exfoliants, compact formulations, or the like.

In certain embodiments, the conditioned media comprises at least one culture-derived growth factor, the at least one growth factor comprising at least one of: vascular endothelial growth factor (VEGF), transforming growth factor beta (TGFβ), hepatocyte growth factor (HGF), keratinocyte growth factor (KGF), interleukin-3 (IL-3), IL-6, or IL-8; and at least one culture-derived antioxidant, the at least one antioxidant comprising at least one of: glutathione, glutathione peroxidase, glutathione reductase, glutathione disulfide, catalase, superoxide dismutase, alpha-tocopherol, gamma-tocopherol, ubiquinol-9, ubiquinone 9, ascorbic acid, cysteine, or cystine. In certain embodiments, the compositions further comprise at least one extracellular matrix component, such as soluble collagen, for example, but not limited to collagen type I or collagen type III.

In certain embodiments, the methods comprise combining a pre-conditioned medium with a three-dimensional culture under appropriate conditions to generate a conditioned medium comprising at least one culture-derived growth factor, the at least one growth factor comprising at least one of: vascular endothelial growth factor (VEGF), transforming growth factor beta (TGFβ), hepatocyte growth factor (HGF), keratinocyte growth factor (KGF), interleukin-3 (IL-3), IL-6, or IL-8; and at least one culture-derived antioxidant, the at least one antioxidant comprising at least one of: glutathione, glutathione peroxidase, glutathione reductase, glutathione disulfide, catalase, superoxide dismutase, alpha-tocopherol, gamma-tocopherol, ubiquinol-9, ubiquinone 9, ascorbic acid, cysteine, or cystine. According to the methods of the invention, the conditioned media or an extract thereof are combined with an acceptable carrier to form a composition. In certain embodiments, the composition is a cosmeceutical composition and the acceptable carrier is a cosmeceutically-acceptable carrier. In certain embodiments, the three-dimensional culture comprises eukaryotic cells, particularly human dermal fibroblasts, keratinocytes, chondrocytes, smooth muscle cells, and the like.

DETAILED DESCRIPTION OF EXEMPLARY EMBODIMENTS

Figure 1:
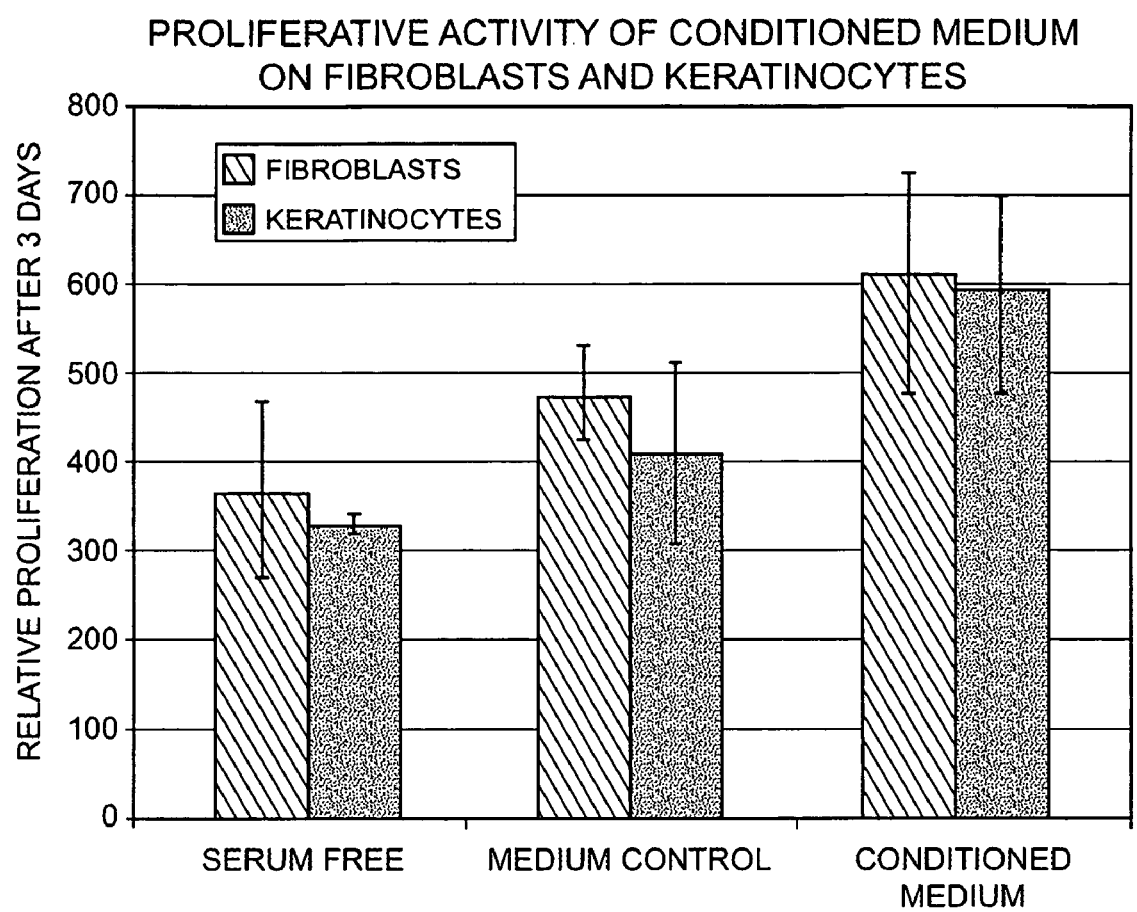
FIG. 1 graphically depicts the effect of serum-free medium, pre-conditioned media, or conditioned media on the in vitro proliferation of fibroblast or keratinocyte cultures. Fibroblast proliferation is shown in solid bars with error bars. Keratinocyte proliferation is shown in gray stippled bars with error bars.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

The section headings used herein are for organizational purposes only and are not to be construed as limiting the subject matter described. All references cited in this specification are expressly incorporated by reference, in their entirety, for any purpose.

The term "culture-derived" as used herein refers to a component of conditioned cell culture media that is not present in the starting cell culture media that is used to culture and feed the cells, but is produced by the cultured cells and enters the media. For example, vascular epithelial growth factor (VEGF) is present in conditioned cell culture media obtained from three-dimensional cultures of human fibroblasts, while VEGF is not typically present in the original pre-conditioned cell culture media ("pre-conditioned media") prior to conditioning. Thus, VEGF is secreted into the media by the cells. Also within the meaning of the term culture-derived are compounds that are initially present in the pre-conditioned media, but whose concentration is increased during the culture process. For example, but not as a limitation, if the original pre-conditioned media comprises 1 ng/ml VEGF and the same media after conditioning comprises 5 ng/ml VEGF, then the conditioned media comprises culture-derived VEGF.

The term "growth factor" as used herein refers to a protein, a polypeptide, or a complex of polypeptides, including cytokines, that are produced by a cell and which can effect itself and/or a variety of other neighboring or distant cells. Typically growth factors affect the growth and/or differentiation of specific types of cells, either developmentally or in response to a multitude of physiological or environmental stimuli. Some, but not all, growth factors are hormones. Exemplary growth factors are insulin, insulin-like growth factor (IGF), nerve growth factor, VEGF, keratinocyte growth factor (KGF), fibroblast growth factors (FGFs), including basic FGF (bFGF), platelet-derived growth factors (PDGFs), including PDGF-AA and PDGF-AB, hepatocyte growth factor (HGF), transforming growth factor alpha (TGFα), transforming growth factor beta (TGFβ), including TGFβ$_1$ and TGFβ$_3$, epidermal growth factor (EGF), granulocyte-macrophage colony-stimulating factor (GM-CSF), granulocyte colony-stimulating factor (G-CSF), interleukin-6 (IL-6), IL-8, and the like. Growth factors are discussed in, among other places, Molecular Cell Biology, Scientific American Books, Darnell et al., eds., 1986; The Molecular and Cellular Biology of Wound Repair, Clark, Plenum Press, 1996; and Principles of Tissue Engineering, 2d ed., Lanza et al., eds., Academic Press, 2000. The skilled artisan will understand that any and all culture-derived growth factors in the conditioned media described herein are within the scope of the invention.

The term antioxidant is used in the broad sense herein and encompasses any substance that slows down or prevents oxidation or free radical formation. Thus, antioxidants include enzymes and other compounds that are able to counteract, at least in part, the damaging effects of free radicals produced by, among other things, ultraviolet light and environmental pollutants, in tissues such as, but not limited to, the skin. For example, the antioxidant defense system of the skin includes antioxidant enzymes and a group of low molecular weight antioxidants (LMWA). The LMWA have been shown to prevent oxidative damage, at least in part, by interacting with radical oxygen species, either directly or indirectly. Exemplary antioxidants are cysteine, glutathione, glutathione disulfide, glutathione peroxidase, glutathione reductase, catalase, vitamin E, including alpha- and gamma-tocopherol, ascorbic acid, ubiquinol 9, ubiquinone 9, and the like. Discussions of antioxidants may be found in, among other places, Kohen et al., Toxicology 148: 149–157 (2000); Kohen, Biomed. Pharmacother. 53: 181–192 (1999); Kohen et al., Methods of Enzymol. 300: 285–90, Academic Press (1999); Miyachi, Dermatol. Sci. 9:79–86 (1995); and Stohs, J. Basic Clin. Physio. Pharmacol. 6:206–228 (1995). The skilled artisan will understand that any and all culture-derived antioxidants in the conditioned media described herein are within the scope of the invention.

The skilled artisan will readily understand what is meant by terminology such as "treated with an amount of IL-1α sufficient to enhance the expression of KGF" or "treated with an amount of PDGF sufficient to enhance the expression of VEGF." Additionally, the skilled artisan will be able to determine whether the expression of a particular growth factor has been induced or enhanced by performing an appropriate assay. Exemplary assays include ELISA, western blot, polyacrylamide gel electrophoresis, HPLC, or the like, using appropriate markers, standards, and/or commercially-available kits, as appropriate. For example, ELISA kits for the quantitation of VEGF, KGF, or various other growth factors are commercially available from R & D Systems, Minneapolis, Minn.

The term extracellular matrix ("ECM") encompasses essentially all secreted molecules that are immobilized outside of the cell. In vivo, the ECM provides order in the extracellular space and serves functions associated with establishing, separating, and maintaining differentiated tissues and organs. The ECM is a complex structure that is found, for example, in connective tissues and basement membranes, also referred to as the basal lamina. Connective tissue typically contains isolated cells surrounded by ECM that is naturally secreted by the cells. Components of the ECM have been shown to interact with and/or bind growth and differentiation factors, cytokines, matrix metalloproteases (MMPs), tissue inhibitors of metalloproteases (TIMPs), and other soluble factors that regulate cell proliferation, migration, and differentiation. Descriptions of the ECM and its components may be found in, among other places, Guidebook to the Extracellular Matrix, Anchor, and Adhesion Proteins, 2d ed., Kreis and Vale, eds., Oxford University Press, 1999 ("Kreis et al."); Geiger et al., Nature Reviews Molecular Cell Biology 2:793–803, 2001; Iozzo, Annual Review of Biochemistry, 1998, Annual Reviews, Palo Alto, Calif.; Boudreau and Jones, Biochem. J. 339: 481–88, 1999; Extracellular Matrix Protocols, Streuli and Grant, eds., Humana Press 2000; Metzler, Biochemistry the Chemical Reactions of Living Cells, 2d ed., vol. 1, 2001, Academic Press, San Diego, particularly chapter 8; and Lanza et al., particularly chapters 4 and 20.

Certain embodiments include at least one component of the ECM. In certain embodiments, the extracellular matrix component comprises at least one of: at least one protein, at least one glycoprotein, at least one proteoglycan, and at least one glycosaminoglycan. Exemplary glycoproteins, proteoglycans, and glycosaminoglycans include but are not limited to, collagen type I, collagen type II, collagen type III, collagen type IV, collagen type V, collagen type VI, collagen type VII, collagen type VIII, collagen type IX, collagen type X, collagen type XI, collagen type XII, collagen type XIII, collagen type XIV, collagen type XV, collagen type XVI, collagen type XVII, collagen type XVIII, fibronectin, laminin, particularly laminin-1, laminin-2, laminin-4, and laminin-5, lumican, tenascin, versican, perlecan, thrombospondin, particularly thrombospondin-2 and thrombospondin-4, or laminin, particularly laminin-1, -2, -4, and -5, agrin, nidogen, bamacan, decorin, biglycan, fibromodulin, elastin, fibrillin, hyaluronan, vitronectin, chondroitin sulphate, dermatan sulphate, heparan sulphate, and keratan sulphate.

The term "extract" when used in reference to conditioned cell culture media refers to any subcomponent of fraction of the conditioned media, whether obtained by dialysis, fractionation, distillation, phase separation, gel filtration chromatography, affinity chromatography, hollow fiber filtration, precipitation, concentration, or the like.

The term "substantially free from," when used in reference phenol red, "components of bovine-origin," or "non-human animal products" refers to conditioned media or extracts thereof that contain little to no phenol red, little to no components of bovine-origin, little or no non-human animal products, or combinations thereof. In certain embodiments, the conditioned cell culture media comprises less than 49.999%, 30%, 20%, 10%, 5%, 1%, 0.5%, 0.05%, or no (0%) phenol red. In certain embodiments, the conditioned media comprises less than 49.999%, 30%, 20%, 10%, 5%, 1%, 0.5%, 0.05%, or no (0%) components of bovine-origin. Exemplary media components of bovine-origin include fetal calf serum, calf serum, bovine serum, bovine collagen, bovine insulin, bovine transferrin, and the like. In certain embodiments, the conditioned media comprises less than 49.999%, 30%, 20%, 10%, 5%, 1%, 0.5%, 0.05%, or no (0%) non-human animal products. In addition to the exemplary components of bovine-origin, listed above, non-human animal products include any animal products not of human origin, such as tissue culture components and products of porcine-origin. The skilled artisan will know that "serum-free" media and animal product-free media is commercially available from several vendors of cell culture media. Likewise, phenol red free media is also commercially available or can be prepared.

The term cosmeceutical refers to a formulation or composition comprising at least one biologically active ingredient that has an effect on the user of the product and at least one cosmeceutically-acceptable carrier. Cosmeceuticals may be viewed as cosmetics that, in certain applications and under appropriate conditions, may provide medicinal or drug-like benefits. In certain applications, for example, cosmeceuticals may affect the underlying structure of the skin, decrease wrinkle depth, or reverse or ameliorate the effect of photooxidation or aging on the skin. Cosmeceuticals may be particularly useful as skin care products, hair care products, and sun care products. In certain embodiments, cosmeceutical compositions comprise delivery systems including at least one of liposomes, cyclodextrins, polymer systems, or hyaluronic acid or related compounds. Cosmeceutical compositions comprise cosmeceutically-acceptable carriers. The skilled artisan will understand that a pharmaceutically-acceptable carrier or formulation that is suitable for topical applications will typically also be a cosmeceutically-acceptable carrier or formulation.

A topical cosmetic or cosmeceutical ointment, lotion, or gel composition typically contains a concentration of active ingredients comprising conditioned media or extracts thereof, from about 1 to 99%, about 5 to 95%, about 20 to 75%, or about 5 to 20%, in a cosmetically-acceptable carrier or a cosmeceutically-acceptable carrier, such as a pharmaceutical cream base, an oil-in-water emulsion, a water-in-oil emulsion, a gel, or the like. Various cosmetic and cosmeceutical compositions for topical use include drops, tinctures, lotions, creams, salves, serums, solutions, and ointments containing conditioned media or extracts, and an appropriate carrier. The optimal percentage of the conditioned media or extract in each composition varies according to the composition's formulation and the therapeutic effect desired.

The skilled artisan in the formulation arts will understand that the inventive compositions may comprise any of a number of cosmetically-, cosmeceutically-, or pharmaceutically-acceptable formulations, depending on the type of product, the nature of the composition, the location of composition's use, the desired effect, and the like. While proprietary formulations are common in the formulation arts, formulators of ordinary skill will be able to determine or readily select appropriate formulations for specific applications without undue experimentation.

The skilled artisan will understand that the appropriate carriers of the inventive compositions typically will contain ingredients, such as those typically found in the cosmetic and cosmeceutical fields: oils, waxes or other standard fatty substances, or conventional gelling agents and/or thickeners; emulsifiers; moisturizing agents; emollients; sunscreens; hydrophilic or lipophilic active agents, such as ceramides; agents for combatting free radicals; bactericides; sequestering agents; preservatives; basifying or acidifying agents; fragrances; surfactants; fillers; natural products or extracts of natural product, such as aloe or green tea extract; vitamins; or coloring materials. The amounts of these various ingredients will vary depending on the use of the composition and the cosmetic or cosmeceutical effect desired.

Discussions of cosmetic- and cosmeceutically-acceptable ingredients and formulations may be found in, among other places, FDA Cosmetics Handbook, U.S. Food and Drug Administration; Handbook of Cosmetic and Personal Care Additives, Ash and Ash, compilers, 1994, Chemical Publishing, New York, N.Y.; Bennett's Cosmetic Formulary, 1993, Chemical Publishing Co.; Harry's Cosmeticology, 7$^{th}$ ed., Wilkinson & Moore, 1982 and 8$^{th}$ ed., Rieger, 2000, Chemical Publishing; Cosmetic Bench Reference-2001, Allerud Publishing Corp.; CTFA Compendium of Cosmetic Ingredient Composition, Nikitakis and McEwen, eds., 1990, Cosmetic, Toiletry, and Fragrance Association, Washington, D.C., Surfactant Encyclopedia, 2$^{nd}$ revised edition, Rieger, 1996, Allured Publishing; The Chemistry and Manufacture of Cosmetics, 2$^{nd}$ ed., De Navarre, Van Nostrand, Princeton, N.J.; Encyclopedia of Common Natural Ingredients Used in Food, Drugs, and Cosmetics, Leung, 1996, John Wiley; A Consumer's Dictionary of Cosmetic Ingredients, 5$^{th}$ ed., Winter, 1999, Three Rivers Press, New York, N.Y.; Cosmeceuticals: Active Skin Treatment, 1998, Allured Publishing; Handbook of Cosmetic Science and Technology, Knowlton and Pearce, 1993, Elsevier Advanced Technology, Oxford, UK; Personal-Care Formulas, 1997, Allured Publishing; Beginning Cosmetic Chemistry, Scheuller and Romanowski, 1999, Allured Publishing; and Skin Permeation: Fundamentals and Application, Zatz, 1993, Allured Publishing. Discussions of pharmaceutically-acceptable ingredients and formulations may be found in, among other places, Remington's Pharmaceutical Sciences, 18$^{th}$ ed., Gennaro, ed., 1990, Mack Publishing.

In certain embodiments, the conditioned media is generated using pre-conditioned media that is serum-free or animal product-free. Serum-free and animal product-free (sometimes referred to as protein-free) media is commercially available from, among other vendors, LifeTechnologies-GibcoBRL, Rockville, Md.; Sigma-Aldrich, Saint Louis, Mo.; or BioWhittaker, Walkersville, Md.). Exemplary serum-free media include: UltraCULTURE™, UltraDOMA™ and UltraCHO™, from BioWhittaker; Serum-free Hybridoma Medium, CHO Serum-free Medium, and MDCK Serum-free Medium, from Sigma-Aldrich; and Keratinocyte-SFM (KSFM), AIM V® Media, StemPro®-34 SFM, Human Endothelial-SFM, Macrophage-SFM, and HepatoZYME-SFM from Life Technologies. Exemplary protein-free media include: UltraDOMA-PF™ from BioWhittaker; Animal Component-free Hybridoma Medium, Serum-free and Protein-free Hybridoma Medium HybriMax®, CHO Protein-free Medium, Chemically-defined CHO Medium, and MDCK Protein-free Medium from Sigma-Aldrich; and Defined Keratinocyte-SFM from Life Technologies. The skilled artisan will appreciate that the use of serum-free media for mammalian cell culture is well established, and is described in, among other places, Cold Spring Harbor Conferences on Cell Proliferation, Vol. 9, Sato et al., eds., (1982) Cold Spring Harbor Laboratory, Cold Spring Harbor, N.Y.; Barnes et al., Anal. Biochem. 102, 255 (1980); BioWhittaker 1999/2000 catalog, pp. 42–51; Barnes, Serum-Free Animal Cell Culture, BioTechniques 5(6):534–42; and Freshney, Culture of Animal Cells, 3d ed., Wiley-Liss, New York, N.Y., 1994.

In certain embodiments, a three-dimensional cell culture comprises a scaffold or framework. Three-dimensional cell culture frameworks are described in, among other places, U.S. Pat. Nos. 4,963,489; 5,460,939; and U.S. application Ser. No. 09/137,567; see also, Pachence and Kohn, Biodegradable Polymers, pp. 263–77, in Principles of Tissue Engineering, 2d ed., Lanza et al., eds., Academic Press, 2000 (describing suitable materials and selection criteria). In other embodiments, a three-dimensional cell culture comprises a collagen matrix, including contracted collagen gels; a gelatin matrix; or a gel matrix. In certain embodiments, the collagen matrix comprises human collagen. In certain embodiments, the collagen matrix comprises bovine collagen, porcine collagen, rat collagen, or combinations thereof. Collagen gels for use as hydrogel scaffolds are described in, among other places, Pachence and Kohn, Biodegradable Polymers, pp. 263–77, in Principles of Tissue Engineering, 2d ed., Lanza et al., eds., Academic Press, 2000; and Parenteau, The First Tissue-Engineered Products, Scientific American 280:83–84,1999. See generally, Principles of Tissue Engineering, Lanza et al., eds., R. G. Landes Co. and Academic Press, 1997; and Principles of Tissue Engineering, 2d ed., Lanza et al., eds., Academic Press, 2000.

In certain embodiments, the conditioned media comprises at least one genetically-engineered growth factor, at least one genetically-engineered antioxidant, and/or at least one genetically-engineered extracellular matrix component, wherein the at least one growth factor or antioxidant includes a heterologous peptide sequence that is capable of enhancing cell penetration, also referred to as protein transduction. A heterologous peptide sequence is a contiguous string of amino acids that are not found in the naturally-occurring growth factor or antioxidant. Rather, the heterologous peptide has been introduced into the naturally-occurring growth factor or antioxidant, typically at or near the amino terminus or the carboxy terminus, using a conventional molecular biology technique such as genetic engineering. Such a "transport-enhanced" growth factor, antioxidant, or extracellular matrix component may, under appropriate conditions, penetrate the cell more readily or more quickly than its naturally-occurring counterpart. Exemplary heterologous peptides known to enhance cell membrane permeation or transport are shown in Table 1 below.

TABLE 1

Exemplary Transport Peptides

| Amino Acid Sequence | Identity | Reference |
|---|---|---|
| Arg-Gln-Ile-Lys-Ile-Trp-Phe-Gln-Asn-Arg-Arg-Met-Lys-Trp-Lys-Lys (SEQ ID NO:1) | Antennapedia homeodomain (43-58) | Derossi et al. |
| Arg-Gln-Ile-Lys-Ile-Trp-Phe-Pro-Asn-Arg-Arg-Met-Lys-Trp-Lys-Lys (SEQ ID NO:2) | Pro 50 | Derossi et al. |
| Arg-Lys-Lys-Arg-Arg-Gln-Arg-Arg-Arg (SEQ ID NO:3) | HIV-1 Tat transduction domain (49-57) | Kwon et al. |

TABLE 1-continued

Exemplary Transport Peptides

| Amino Acid Sequence | Identity | Reference |
|---|---|---|
| Gly-Trp-Thr-Leu-Asn-Ser-Ala-Gly-Tyr-Leu-Leu-Gly-Lys-Ile-Asn-Leu-Lys-Ala-Leu-Ala-Ala-Leu-Ala-Lys-Lys-Ile-Leu (SEQ ID NO:4) | Transportan | Pooga et al. |
| Thr-Arg-Gln-Ala-Arg-Arg-Asn-Arg-Arg-Arg-Trp-Arg-Glu-Arg-Gln-Arg (SEQ ID NO:5) | HIV-1 Rev (34-50) | Futaki et al. |
| Arg-Arg-Arg-Arg-Asn-Arg-Thr-Arg-Arg-Asn-Arg-Arg-Val-Arg (SEQ ID NO:6) | FHV coat (35-49) | Futaki et al. |
| Lys-Met-Thr-Arg-Ala-Gln-Arg-Arg-Ala-Ala-Ala-Arg-Arg-Asn-Arg-Trp-Thr-Ala-Arg (SEQ ID NO:7) | BMV Gag (7-25) | Futaki et al. |
| Thr-Arg-Gln-Arg-Thr-Arg-Arg-Ala-Arg-Arg-Asn-Arg (SEQ ID NO:8) | HTLV-II Rex (4-16) | Futaki et al. |
| Lys-Leu-Thr-Arg-Ala-Gln-Arg-Arg-Ala-Ala-Ala-Arg-Lys-Asn-Lys-Arg-Asn-Thr-Arg (SEQ ID NO:9) | CCMV Gag (7-25) | Futaki et al. |
| Asn-Ala-Lys-Thr-Arg-Arg-His-Glu-Arg-Arg-Arg-Lys-Leu-Ala-Ile-Glu-Arg (SEQ ID NO:10) | P22 N (14-30) | Futaki et al. |
| Met-Asp-Ala-Gln-Thr-Arg-Arg-Arg-Glu-Arg-Arg-Ala-Glu-Lys-Gln-Ala-Gln-Trp-Lys-Ala-Ala-Asn (SEQ ID NO:11) | γN (1-22) | Futaki et al. |
| Thr-Ala-Lys-Thr-Arg-Tyr-Lys-Ala-Arg-Arg-Ala-Glu-Leu-Ile-Ala-Glu-Arg-Arg (SEQ ID NO:12) | Φ21 N (12-29) | Futaki et al. |
| Thr-Arg-Arg-Asn-Lys-Arg-Asn-Arg-Lys-Gln-Glu-Gln-Leu-Asn-Leu-Lys (SEQ ID NO:13) | Yeast PRP6 (129-144) | Futaki et al. |
| Lys-Arg-Arg-Ile-Arg-Arg-Glu-Arg-Gln-Lys-Met-Ala-Ala-Ala-Lys-Ser-Arg-Asn-Arg-Arg-Arg-Glu-Leu-Thr-Asp-Thr (SEQ ID NO:14) | Human cFos (139-164) | Futaki et al. |
| Gly-Arg-Lys-Lys-Arg-Arg-Gln-Arg-Arg-Arg-Pro-Pro-Gln (SEQ ID NO:15) | D-Tat | Futaki et al. |
| Gly-Arg-Arg-Arg-Arg-Arg-Arg-Arg-Arg-Arg-Pro-Pro-Gln (SEQ ID NO:16) | $R_9$-Tat | Futaki et al. |
| Arg-Ile-Lys-Ala-Glu-Arg-Lys-Arg-Met-Arg-Asn-Arg-Ile-Ala-Ala-Ser-Lys-Ser-Arg-Lys-Arg-Lys-Leu-Glu-Arg-Ile-Ala-Arg (SEQ ID NO:17) | Human cJun (252-279) | Futaki et al. |
| Arg-Arg-Arg-Arg-Arg-Arg (SEQ ID NO:18) | $R_6$ | Futaki et al. |
| Lys-Arg-Ala-Arg-Asn-Thr-Glu-Ala-Ala-Arg-Arg-Ser-Arg-Ala-Arg-Lys-Leu-Gln-Arg-Met-Lys-Gln (SEQ ID NO:19) | Yeast GCN4 (231-252) | Futaki et al. |

The person of skill in the art will realize that although the transport peptides shown in Table 1 typically contain L-amino acids, transport peptides comprising D-amino acids, in whole or in part, such as D43-58 (Derossi et al.), are also within the scope of the invention. Such peptides may have the benefit of being more stable, for example, less susceptible to proteolysis than the L-enantiomer. The skilled artisan will appreciate that a genetically-engineered construct comprising a nucleic acid sequence encoding transport peptide, for example, but not limited to, one of the peptides shown in Table 1 (with or without D-amino acid residues) operatively linked to a nucleic acid sequence encoding a growth factor, an antioxidant, or an extracellular matrix component, would produce a transport-enhanced growth factor, transport-enhanced antioxidant, or transport-enhanced extracellular matrix component, either inducibly or constitutively depending on the construct. Such genetically-engineered constructs, when operatively linked to appropriate regulatory sequences, such as one or more promoter, one or more enhancer, a polyA encoding sequence, and a termination sequence, could under appropriate conditions be used to stably transform eukaryotic cells, including, but not limited to human cells, using methods known in the art. These stably transformed cells could be used to seed three-dimensional frameworks, collagen gels, or the like, and then propagated using conventional methods to generate a three-dimensional culture. The conditioned media from these cultures would, under appropriate conditions, comprise the transport-enhanced growth factor, transport-enhanced antioxidant, and/or transport-enhanced extracellular matrix component.

Examples of transport enhancing peptides and methods of genetically-engineering transport-enhanced molecules may be found in, among other places, Stephens et al., Proc. Natl. Acad. Sci., in press (2001) (www.pnas.org.cgi/doi/pnas.081065198); Schwarze et al., Trends in Cell Biology, 10:290–95 (2000); Falwell et al., Proc. Natl. Acad. Sci. 91:664–68 (1994); Pooga et al., FASEB J. 12:67–77 (1998); Vivés et al., J. Biol. Chem. 272:16010–17 (1997); Derossi et al., J. Biol. Chem. 271:18188–93 (1996); Kwon et al., FEBS Letters 485:163–67 (2000); Barka et al., J. Histochem. Cytochem. 48:1453–60 (2000); Steffen, Methods in Mol. Biol. 161:141–148 (2001); and Futaki et al., J. Biol. Chem. 276:5836–40 (2001).

Descriptions of conventional molecular biology techniques and protocols may be found in, among other places, Ausbel et al., Current Protocols in Molecular Biology, John Wiley & Sons, Inc. (1995, including supplements through Jun. 7, 2001)("Ausbel et al."); Sambrook et al., Molecular Cloning: A Laboratory Manual, 2 ed., Cold Spring Harbor Press (1989)("Sambrook et al."); Sambrook and Russell, Molecular Cloning: A Laboratory Manual, 3 ed., Cold Spring Harbor Press (2001)("Sambrook and Russell").

The term "transport-enhanced growth factor", "transport-enhanced antioxidant", or "transport-enhanced extracellular matrix component" as used herein refers to any protein or polypeptide having the growth factor, antioxidant, or extracellular matrix component properties, respectively, as the corresponding naturally-occurring growth factor, antioxidant, or extracellular matrix component, other than cell permeation or transport. For example, but not limited to, transport-enhanced VEGF and naturally-occurring VEGF. A specific transport-enhanced growth factor or transport-enhanced antioxidant refers to (1) an amino acid sequence encoded by a gene fragment encoding a specific growth factor or a specific antioxidant fused to a gene fragment encoding a transport peptide, and biologically active peptide or polypeptide fragments derived therefrom, (2) naturally-occurring allelic variants of the gene fragment which result in one or more amino acid substitutions, deletions, and/or insertions as compared to the corresponding naturally-occurring growth factor or antioxidant and/or (3) chemically modified derivatives as well as nucleic acid and or amino acid sequence variants thereof as provided for herein.

As used herein, the term "transport-enhanced growth factor fragment" or "transport-enhanced antioxidant fragment" refers to a peptide or polypeptide that contains less than the full length amino acid sequence of naturally occurring transport-enhanced growth factor or transport-enhanced antioxidant, but has substantially the same biological activity as transport-enhanced growth factor or transport-enhanced antioxidant. Such a fragment may be truncated at the amino terminus, the carboxy terminus, and/or internally, and may be chemically modified.

As used herein, the term "transport-enhanced growth factor derivative" or "transport-enhanced growth factor variant" refers to a transport-enhanced growth factor, or fragment that 1) has been chemically modified, as for example, by addition of one or more polyethylene glycol molecules, sugars, phosphates, or other such molecules not naturally attached to naturally-occurring growth factor, and/or 2) contains one or more nucleic acid or amino acid sequence substitutions, deletions, and/or insertions as compared to the naturally-occurring growth factor. As used herein, the term "transport-enhanced antioxidant derivative" or "transport-enhanced antioxidant variant" refers to a transport-enhanced antioxidant, or fragment that 1) has been chemically modified, as for example, by addition of one or more polyethylene glycol molecules, sugars, phosphates, or other such molecules not naturally attached to the corresponding naturally-occurring antioxidant, and/or 2) contains one or more nucleic acid or amino acid sequence substitutions, deletions, and/or insertions as compared to the naturally-occurring antioxidant.

Percent sequence identity can be determined by standard methods that are commonly used to compare the similarity in position of the amino acids of two polypeptides. By way of example, using a computer program such as BLAST or FASTA, the two polypeptides for which the percent sequence identity is to be determined are aligned for optimal matching of their respective amino acids (the "matched span", which can include the full length of one or both sequences, or a pre-determined portion of one or both sequences). Each computer program provides a "default" opening penalty and a "default" gap penalty, and a scoring matrix such as PAM 250. A standard scoring matrix (see Dayhoff et al., in: Atlas of Protein Sequence and Structure, vol. 5, supp.3 (1978)) can be used in conjunction with the computer program. The percent identity can then be calculated by determining the percent identity using an algorithm contained in a program such as FASTA: ##EQU1##

Polypeptides that are at least 70 percent identical will typically have one or more amino acid substitutions, deletions, and/or insertions as compared with the corresponding naturally-occurring growth factor or antioxidant. Usually, the substitutions will be conservative so as to have little or no effect on the overall net charge, polarity, or hydrophobicity of the protein but optionally may increase the activity of the transport-enhanced growth factor or transport-enhanced antioxidant. Conservative substitutions are set forth in Table 2 below.

TABLE 2

| Conservative Amino Acid Substitutions | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

As used herein, the terms "effective amount", "therapeutically-effective amount", and "cosmeceutically-effective amount" refer to the amount of conditioned media or extract necessary to produce the desired pharmaceutical or cosmeceutical effect.

The transport-enhanced growth factors or transport-enhanced antioxidants that have use in practicing the present invention may be naturally occurring full length polypeptides, or truncated polypeptides or peptides (i.e, "fragments"). The polypeptides or fragments may be chemically modified, i.e., glycosylated, phosphorylated, and/or linked to a polymer, as described below. In addition, the polypeptides or fragments may be variants of the corresponding naturally-occurring growth factors or antioxidants (i.e., may contain one or more amino acid deletions, insertions, and/or substitutions as compared with naturally-occurring growth factor or antioxidant).

The full length transport-enhanced growth factor or fragments thereof or full length transport-enhanced antioxidant or fragments thereof can be prepared using well known recombinant DNA technology methods. Alternatively, a gene fragment encoding the transport-enhanced growth factor or fragment, or the transport-enhanced antioxidant or fragment may be prepared by chemical synthesis using methods well known to the skilled artisan such as those described by Engels et al. (Angew. Chem. Intl. Ed., 28:716–734 (1989)). These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the transport-enhanced growth factor or transport-enhanced antioxidant will be several hundred nucleotides in length. Nucleic acids larger than about 100 nucleotides can be synthesized as several fragments using these methods. The fragments can then be ligated together to form the full length transport-enhanced growth factor of the transport-enhanced antioxidant. In certain embodiments, the DNA fragment encoding the amino terminus of the polypeptide will have an ATG, which encodes a methionine residue. This methionine may or may not be present on the mature form of the transport-enhanced growth factor or transport-enhanced antioxidant.

In some cases, it may be desirable to prepare nucleic acid and/or amino acid variants of naturally-occurring growth factor or antioxidant. Nucleic acid variants (wherein one or more nucleotides are designed to differ from the wild-type or naturally-occurring growth factor or antioxidant) may be produced using site directed mutagenesis or PCR amplification where the primer(s) have the desired point mutations (see Sambrook et al., Sambrook and Russell, and Ausubel et al., for descriptions of mutagenesis techniques). Chemical synthesis using methods described by Engels et al., supra, may also be used to prepare such variants. Other methods known to the skilled artisan may be used as well. Preferred nucleic acid variants are those containing nucleotide substitutions accounting for codon preference in the host cell that is to be used to produce the transport-enhanced growth factor or transport-enhanced antioxidant. Other preferred variants are those encoding conservative amino acid changes as described above (e.g., wherein the charge or polarity of the naturally occurring amino acid side chain is not altered substantially by substitution with a different amino acid) as compared to wild type, and/or those designed to either generate a novel glycosylation and/or phosphorylation site(s) on growth factor or antioxidant component of the transport-enhanced protein, or those designed to delete an existing glycosylation and/or phosphorylation site(s) on the growth factor or antioxidant component of the transport-enhanced protein.

The fused gene fragment encoding the transport-enhanced growth factor or the fused gene fragment encoding the transport-enhanced antioxidant can be inserted into an appropriate expression vector for expression in a host cell. The vector is typically selected to be functional in the particular host cell employed (i.e., the vector is compatible with the host cell machinery such that amplification of the fused gene fragment and/or expression of the fused gene fragment can occur).

Typically, the vectors used in any of the host cells will contain 5' flanking sequence (also referred to as a "promoter") and other regulatory elements as well such as an enhancer(s), a transcriptional termination element, a complete intron sequence containing a donor and acceptor splice site, a signal peptide sequence, a ribosome binding site element, a polyadenylation sequence, a polylinker region for inserting the nucleic acid encoding the polypeptide to be expressed, and a selectable marker element. Each of these elements are discussed below. Optionally, the vector may contain a "tag" sequence, i.e., an oligonucleotide sequence located at the 5' or 3' end of the transport-enhanced growth factor or transport-enhanced antioxidant coding sequence that encodes polyHis (such as hexaHis) or another small immunogenic sequence. This tag will be expressed along with the protein, and can serve as an affinity tag for purification of the transport-enhanced growth factor or transport-enhanced antioxidant from the host cell. Optionally, the tag can subsequently be removed from the purified transport-enhanced growth factor or transport-enhanced antioxidant by various means such as using an appropriate peptidase.

The 5' flanking sequence may be homologous (i.e., from the same species and/or strain as the host cell), heterologous (i.e., from a species other than the host cell species or strain), hybrid (i.e., a combination of 5' flanking sequences from more than one source), synthetic, or it may be the native growth factor or antioxidant 5' flanking sequence. As such, the source of the 5' flanking sequence may be any eukaryotic cell, typically mammalian cells, preferably human cells, provided that the 5' flanking sequence is functional in, and can be activated by, the host cell machinery.

The 5' flanking sequences useful in the vectors of this invention may be obtained by any of several methods well known in the art. Typically, 5' flanking sequences useful herein other than the naturally-occurring growth factor or antioxidant 5' flanking sequence will have been previously identified by mapping and/or by restriction endonuclease digestion and can thus be isolated from the proper tissue source using the appropriate restriction endonucleases. In some cases, the full nucleotide sequence of the 5' flanking sequence may be known. Here, the 5' flanking sequence may be synthesized using conventional molecular biology methods.

Where all or only a portion of the 5' flanking sequence is known, it may be obtained using PCR and/or by screening a genomic library with suitable oligonucleotide and/or 5' flanking sequence fragments from the same or another species.

Where the 5' flanking sequence is not known, a fragment of DNA containing a 5' flanking sequence may be isolated from a larger piece of DNA that may contain, for example, a coding sequence or even another gene or genes. Isolation may be accomplished by restriction endonuclease digestion using one or more carefully selected enzymes to isolate the proper DNA fragment. After digestion, the desired fragment may be isolated by agarose gel purification, Qiagen® column (Valencia, Calif.) or other methods known to the skilled artisan. Selection of suitable enzymes to accomplish this purpose will be readily apparent to one of ordinary skill in the art.

The transcription termination element is typically located 3' of the end of the transport-enhanced growth factor coding sequence or the transport-enhanced antioxidant coding sequence and serves to terminate transcription of the transport-enhanced growth factor or transport-enhanced antioxidant.

A selectable marker gene element encodes a protein necessary for the survival and growth of a host cell grown in a selective culture medium, such as G418, or a readily identifiable marker, such as green fluorescent protein (GFP).

The ribosome binding element, commonly called the Kozak sequence in eukaryotes, is necessary for translation initiation of mRNA. The element is typically located 3' to the promoter and 5' to the coding sequence of the transport-enhanced growth factor or transport-enhanced antioxidant to be synthesized.

In many cases, transcription of the transport-enhanced growth factor or transport-enhanced antioxidant is increased by the presence of one or more introns on the vector. This is particularly true where the transport-enhanced growth factor or transport-enhanced antioxidant is produced in eukaryotic host cells, especially mammalian host cells. The introns used may be naturally-occurring within the corresponding growth factor or antioxidant sequence, especially where the growth factor or antioxidant sequence used is a full length genomic sequence or a fragment thereof. Where the intron is not naturally-occurring within the growth factor or antioxidant sequence (as for most cDNAs), the intron(s) may be obtained from another source. The position of the intron with respect to the 5' flanking sequence and the growth factor or antioxidant coding sequence is important, as the intron must be transcribed to be effective. As such, where the growth factor or antioxidant nucleic acid sequence is a cDNA sequence, the preferred position for the intron is 3' to the transcription start site, and 5' to the polyA transcription termination sequence. Preferably for growth factor or antioxidant cDNAs, the intron will be located on one side or the other (i.e., 5' or 3') of the growth factor or antioxidant coding sequence such that it does not interrupt the coding sequence. Any intron from any source, including any virus or eukaryotic organism, may be used to practice this invention, provided that it is compatible with the host cell(s) into which it is inserted. Also included herein are synthetic introns. Optionally, more than one intron may be used in the vector.

Where one or more of the elements set forth above are not already present in the vector to be used, they may be individually obtained and ligated into the vector. Methods used for obtaining each of the elements are well known to the skilled artisan and are comparable to the methods set forth above (i.e., synthesis of the DNA, library screening, and the like).

The final vectors used to practice this invention are typically constructed from a starting vectors such as a commercially available vector. Such vectors may or may not contain some of the elements to be included in the completed vector. If none of the desired elements are present in the starting vector, each element may be individually ligated into the vector by cutting the vector with the appropriate restriction endonuclease(s) such that the ends of the element to be ligated in and the ends of the vector are compatible for ligation. In some cases, it may be necessary to "blunt" the ends to be ligated together in order to obtain a satisfactory ligation. Blunting is accomplished by first filling in "sticky ends" using Klenow DNA polymerase or T4 DNA polymerase in the presence of all four nucleotides. This procedure is well known in the art and is described for example in Sambrook et al.

Alternatively, two or more of the elements to be inserted into the vector may first be ligated together (if they are to be positioned adjacent to each other) and then ligated into the vector.

Another method for constructing the vector comprises ligating all of the various elements simultaneously in one reaction mixture. Here, many nonsense or nonfunctional vectors will be generated due to improper ligation or insertion of the elements, however the functional vector may be identified and selected by restriction endonuclease digestion.

Preferred vectors for practicing this invention are those which are compatible with mammalian host cells, particularly human cells. The skilled artisan will know that such vectors may be commercially available. After the vector has been constructed and the gene fragment encoding the transport peptide and the growth factor or antioxidant has been inserted into the proper site of the vector, the completed vector may be inserted into a suitable host cell.

Suitable cells or cell lines may be mammalian cells, preferably human cells such as human dermal fibroblasts, keratinocytes, or other cell types suitable for three-dimensional culture, as described above.

Insertion of the vector into the selected host cell may be accomplished using such methods as calcium chloride precipitation, electroporation, microinjection, lipofection or the DEAE-dextran method. The method selected will in part be a function of the type of host cell to be used. These methods and other suitable methods are well known to the skilled artisan, and are set forth, for example, in Sambrook et al., Sambrook and Russell, or Ausbel et al.

The host cells containing the vector may be cultured using standard media well known to the skilled artisan. The media will usually contain all nutrients necessary for the growth and survival of the cells. The host cells may be transiently transformed or stably transformed, depending on the long term presence of the vector. Typically, stably transformed cells are desired for seeding three-dimensional cultures.

The amount of the transport-enhanced growth factor or transport-enhanced antioxidant produced in the host cell can be evaluated using standard methods known in the art. Such methods include, without limitation, ELISA, Western blot analysis, SDS-polyacrylamide gel electrophoresis, non-denaturing gel electrophoresis, HPLC separation, immunoprecipitation, and the like.

The invention, having been described above, may be better understood by reference to examples. The following examples are intended for illustration purposes only, and should not be construed as limiting the scope of the invention in any way.

EXAMPLE 1

Fibroblast Monolayer Cell Culture

Normal human dermal fibroblasts, isolated from a human foreskin, were cultured in a 150 cm$^2$ tissue culture flasks (Corning, Corning, N.Y.) in monolayer culture using pre-conditioned cell culture media (in this example, high-glucose Dulbecco's Modified Eagle's Media (DMEM; Gibco-BRL, Grand Island, N.Y.) supplemented with 10% bovine calf serum (Hyclone Laboratories, Logan, Utah), nonessential amino acids (GibcoBRL), and 100 U/ml penecillinstreptomycin-250 ng/ml amphoterecin B (GibcoBRL) ("DMEM 1") in a 37° C., 5% $CO_2$ incubator. Monolayer cultures were fed twice weekly with fresh pre-conditioned media and passaged weekly using a 1 to 10 split, as described. See generally, Pinney et al., J. Cell. Physio., 183:74–82 (2000). The dermal fibroblasts may also be expanded in roller bottles with DMEM 1. The conditioned media from these monolayer cultures is collected and saved for future use.

While fibroblast cells have been used for illustrative purposes in this example, the skilled artisan will understand that many other types of cells, for example, but not limited to, other epithelial cell types, endothelial cells, smooth muscle cells, myocytes, keratinocytes, chondrocytes, and the like, may be grown in monolayer culture and in three-dimensional culture.

EXAMPLE 2

Fibroblast Three-Dimensional Culture

Human dermal fibroblasts, for example, from Example 1, can be seeded onto a variety of three-dimensional frameworks or suspended in a collagen matrix, using conventional technology. For example, cells can be seeded onto a bioabsorbable polyglactin mesh framework, such as Vicryl™, a substance commonly used for suture material that is composed of biodegradable mesh fibers of polyglactin 910 (a copolymer of 90:10 polyglycolic acid to polylactic acid) or a three-dimensional lactate/glycolate polymer framework.

Fibroblasts were cultured for approximately two weeks on a three-dimensional lactate/glycolate copolymer framework in antibiotic-free, high-glucose DMEM supplemented with 10% calf serum, 2 mM L-glutamine, non-essential amino acids, and 50 µg/ml ascorbate (J. T. Baker) ("DMEM 2"). In the presence of DMEM 2 and under conditions appropriate for cell growth, the fibroblasts proliferate to fill the interstices of the framework. The cells secrete collagen and other extracellular matrix components, growth factors, and cytokines, among other things, and create a three-dimensional human tissue, such as Dermagraft®, a tissue-engineered product developed for inter alia the treatment of diabetic foot ulcers (Advanced Tissue Sciences, La Jolla, Calif.); see Naughton, Dermal Equivalents, pp. 891–902, in Principles of Tissue Engineering, 2d ed., Lanza et al., eds., Academic Press, 2000.

The cultures were fed every 3–4 days with pre-conditioned DMEM 2 and the conditioned media was collected, starting after day 10, and either tested immediately or frozen at −20° C. for future testing. To quantitate the concentration of various growth factors and cytokines in one preparation of conditioned media, immunoassays were performed using the appropriate commercially available human growth factor ELISA kits (Quantikine® Immunoassays, R & D Systems, Minneapolis, Minn.). Pre-conditioned DMEM 2 was assayed in parallel as a negative (background) control. Although the assays were identified as species specific, certain lots of bovine serum showed low levels of cross-reactivity in the TGFβ ELISA. As shown in Table 3, the conditioned media comprised at least six culture-derived growth factors.

TABLE 3

Growth Factor and Cytokine Concentrations in Conditioned Media (background subtracted)

| Growth Factor | Concentration ng/ml |
| --- | --- |
| VEGF | 3.2 ng/ml |
| G-CSF | 2.3 ng/ml |
| IL-6 | 0.9 ng/ml |
| IL-8 | 3.2 ng/ml |
| KGF | 1.67 ng/ml |
| TGFβ | 0.8 ng/ml |
| EGF | Not Detected |
| FGF | Not Detected |

The skilled artisan will understand that, while these illustrative examples describe DMEM-based pre-conditioned media, depending on the cell type being cultured, many other types of cell culture media may be used. Exemplary cell culture media include Minimum Essential Medium Eagle (MEM), Keratinocyte Medium, Melanocyte Medium, Hepaotcyte Medium, Amniocyte Medium, Bone Marrow Medium, Basal Medium Eagle (BME), BGJb Medium (Fitton-Jackson Modification), Iscove's Modified Dulbecco's Medium (IMDM), L-15 Medium (Liebovitz), McCoy's 5A Modified Medium, MCDB Medium, Medium 199, Ham's F-10 Medium, Ham's F-12 Medium, RPMI-1640, Waymouth Medium, and the like; commercially available from, among others, Sigma-Aldrich, Life Technologies-GibcoBRL, or BioWhittaker.

EXAMPLE 3

Alternative Three-Dimensional Fibroblast Culture

Passage 8 human dermal fibroblasts were seeded into conventional 1750 $cm^2$ corrugated roller bottles (Nalge or Nunc) containing a sterile nylon mesh scaffold (Industrial Fabrics) sitting on or near the inner surface of the roller bottle. The passage 8 fibroblasts were seeded at a density of approximately $4-6 \times 10^7$ cells per roller bottle and cultured in antibiotic-free pre-conditioned media (DMEM (# 078-0521–189, Life Technologies-Gibco), supplemented with 2 mM L-glutamine (Life Technologies), non-essential amino acids (Life Technologies), 56 mg/l L-ascorbic acid (J. T. Baker), and 10% calf serum (HyClone Laboratories)). The roller bottles were incubated at 37° C. in a roller apparatus. The medium in the roller bottles was replaced daily or every other day using the pre-conditioned media described above and the conditioned cell culture media was collected. The VEGF level in the conditioned media was quantitated by ELISA, using the Quantikine human VEGF assay (R & D Systems, Minneapolis, Minn.) according to the manufacturer's instructions.

The conditioned media was pre-filtered to remove large particulate, such as cell debris using a 3M™ 522 High Performance Liquid Filter Bag (Southcoast) with a 2.5 micron rating to produce "filtered media" (also referred to as 1× conditioned media). For certain applications the filtered media was concentrated in a cross flow hollow fiber ultrafiltration cartridge (Model #UFP-10-C-55A, A/G Technology Corp., Needham, Mass.) at a flow rate of 25 liters per minute, according to the manufacturer's Operating Guide. The "nutrient solution," (also referred to as 10× conditioned media) concentrated to approximately three to fifteen times the initial concentration, was collected.

The 1× and 10× conditioned media is used by formulators for preparing compositions comprising cosmetic, cosmeceutical, or pharmaceutical formulations with cosmetically-acceptable, cosmeceutically-acceptable or pharmaceutically-acceptable carriers. The skilled artisan will appreciate that cosmetically-acceptable carriers, cosmeceutically-acceptable carriers and pharmaceutically-acceptable carriers may be the same or different, depending on the intended application of the composition.

The person of skill in the art will understand that although roller bottles are described in this example, any number of bioreactors may be employed with appropriate modifications to the described conditions. The skilled artisan will also understand that any number of methods of processing the conditioned media, for example, but not limited to, chromatography, HPLC, phase separation, spray drying, evaporation, lyophilization, and the like, using methods known in the art.

EXAMPLE 4

Effect of Conditioned Media on Cell Proliferation

To verify that the culture-derived growth factors, such as measured in Example 2, were biologically active, human keratinocytes or fibroblasts were incubated with the conditioned media and their proliferation was measured. Briefly, $5 \times 10^3$ human keratinocytes or human fibroblasts were seeded into wells of a 96-well plate. These cells were fed with either serum-free media, pre-conditioned media, or pre-conditioned media supplemented with 10% (vol/vol) concentrated conditioned medium and incubated for 48 hours. After incubation the cells were freeze lysed and 200 mL of Cyquant dye was added (Molecular Probes, Eugene, Oreg.) and fluorescence was measured in a Cytoflour. EBM controls were used for a baseline. As shown in FIG. 1, in this experiment, the propagation of both keratinocytes and fibroblasts was highest in the conditioned media.

EXAMPLE 5

Antioxidant Effect of Conditioned Media

This example demonstrates the antioxidant activity of conditioned media. Primary epidermal keratinocytes in Keratinocyte SFM (GibcoBRL) are plated at $1 \times 10^5$ cells/cm$^2$ in conventional 12 well tissue culture plates and allowed to incubate overnight in a 37° C., 5% $CO_2$ incubator. The next day the media is replaced with fresh Keratinocyte SFM, DMEM 1, or DMEM 1 supplemented with conditioned media. The plates are returned to the incubator and cultured for 10 days. Cells are washed once in PBS, then dihydrorhodamine 123 (Molecular Probes, Eugene Oreg.) is added to a final concentration of 1 uM using a 1 mM stock solution in DMSO. Dihydrorhodamine 123 intercalates in cell membranes in a non-fluorescent form. When oxidized, this dye is converted to the fluorescent rhodamine derivative. The mean fluorescence is thus a measure of the total intracellular oxidative state. See, Handbook of Fluorescent Probes and Research Products, 8$^{th}$ ed., Chapter 19, Molecular Probes, Eugene, Oreg.; Royall et al., Arch. Biochem. Biophys. 302:348–55 (1993).

Figure 2:
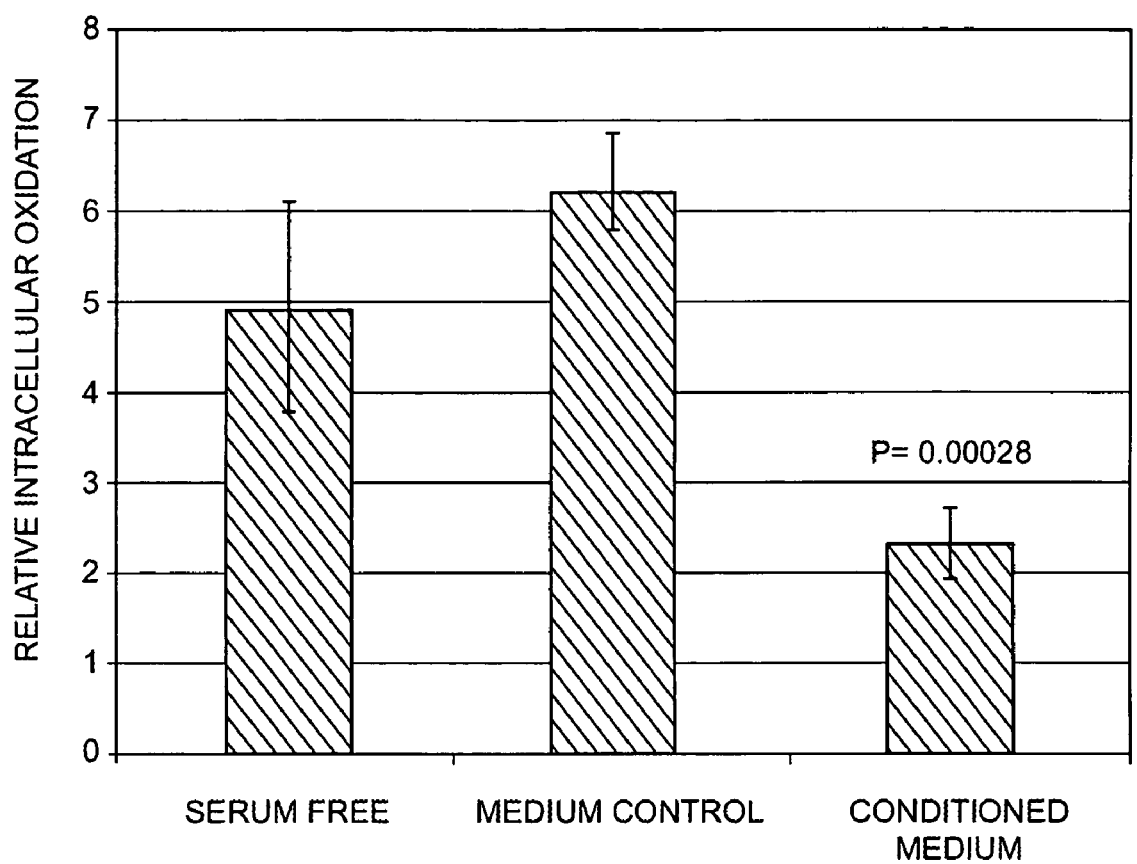
FIG. 2 graphically depicts the antioxidant activity of serum-free medium, control medium (pre-conditioned medium) and conditioned medium on cultured epidermal keratinocytes.

Cells are incubated for an additional 30 minutes in the incubator, then trypsinized and fixed in 2-paraformaldehyde. Fluorescence intensity is measured on a FACScan (Becton-Dickinson). In this experiment, cells grown in conditioned media have a significantly lower intracellular oxidation level compared to cells grown in either the pre-conditioned or the serum-free medium (see FIG. 2).

EXAMPLE 6

HPLC Analysis of Antioxidants in the Conditioned Media

To quantify specific antioxidants present in the cultured media, aliquots of filtered media from Example 3 were analyzed using an HPLC electrochemical detection system (Couloarray Detection System, ESA Inc). The electrochemical detector was set in series with a UV detector for 2-dimensional characterization of compounds and metabolites (Roy et al., Simultaneous Detection of Tocopherols and Tocotrienols in Biological Samples Using HPLC-Coulometric Electrode Array. Meth. Enzymol., 2001 (in press)).

a. Vitamin E (α-Tocopherol and γ-Tocopherol)

Figure 3A:
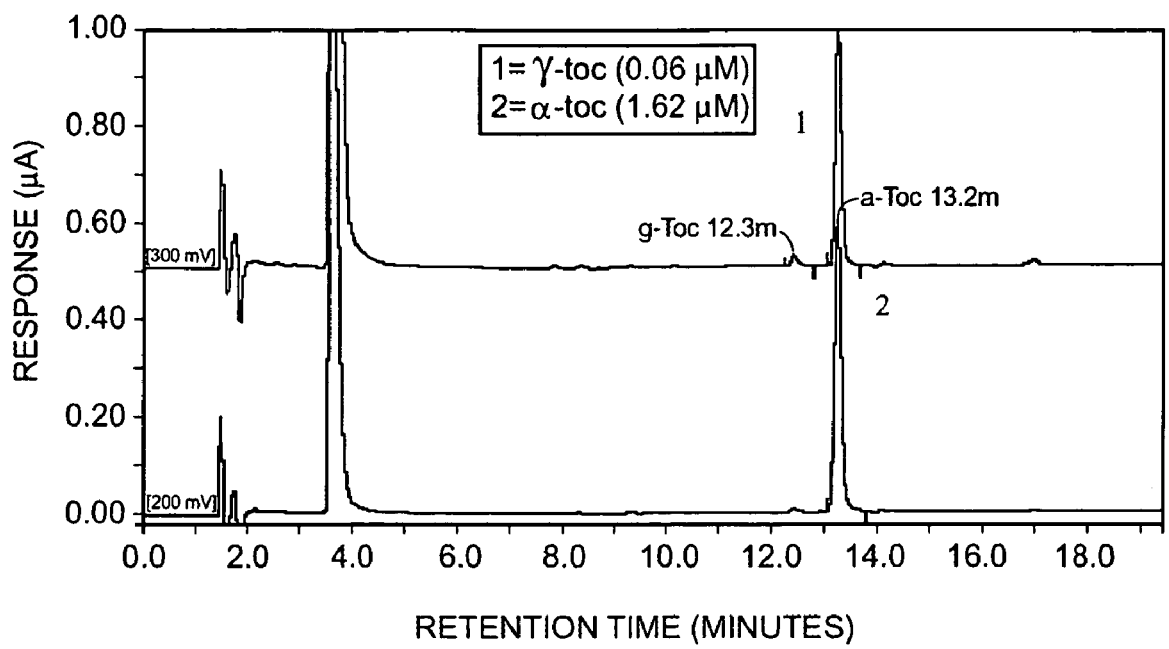
FIG. 3 depicts graphic representations of the measurement of antioxidant levels in filtered medium. Panel 3A shows the results of the HPLC analysis of α-tocopherol and γ-tocopherol, components of Vitamin E. Panel 3B shows the results of the HPLC analysis of glutathione (GSH). Panel 3C shows the results of the HPLC analysis of cysteine. Panel 3D shows the results of the HPLC analysis of cysteine and cystine combined.

Phosphate buffered saline containing 1 mM $Na_2EDTA$, BHT (10 mg/ml) and SDS was added to the sample. The mixture was vigorously vortexed for 15 min at 4° C. and ethanol was added. Vitamin E was extracted in hexane. Hexane phase was collected and dried under nitrogen. Samples were re-dissolved in vitamin E mobile phase and injected to the HPLC system. Authentic compounds were used to generate standard curves, as described (Sen et al., Molecular basis of vitamin E action. Tocotrienol potently inhibits glutamate-induced pp60(c-Src) kinase activation and death of HT4 neuronal cells. J Biol. Chem. 2000 Apr. 28;275(17):13049–55; Roy et al., Simultaneous Detection of Tocopherols and Tocotrienols in Biological Samples Using HPLC-Coulometric Electrode Array. Meth. Enzymol. 2001 (in press)). As shown in FIG. 3A, this filtered media preparation comprised 1.62 µM α-tocopherol and 0.06 µM γ-tocopherol.

b. Glutathione

Figure 3B:
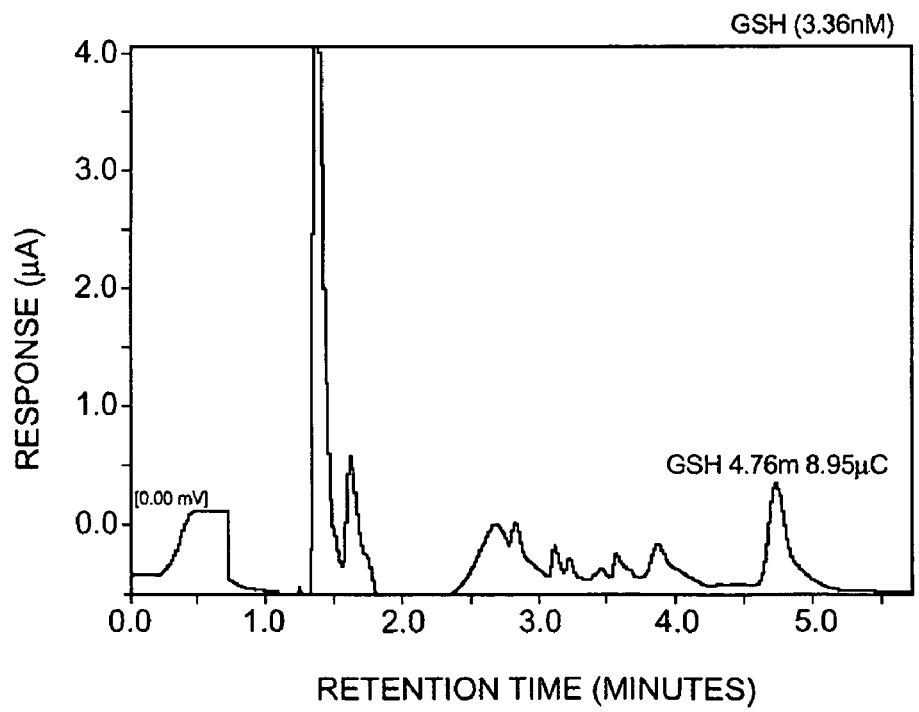

Glutathione (GSH) was extracted from acidified samples and a C-18 column (150 mm×4.6 mm, 5 µm pore size; Alltech, Deerfield, Ill.) was used for GSH separation. HPLC was performed as described (Sen et al., Molecular basis of vitamin E action. Tocotrienol potently inhibits glutamate-induced pp60(c-Src) kinase activation and death of HT4 neuronal cells. J Biol. Chem. 2000 Apr. 28;275(17):13049–55). As shown in FIG. 3B, this filtered media preparation contained 3.36 nM GSH.

c. Cysteine and Cystine

Figure 3C:
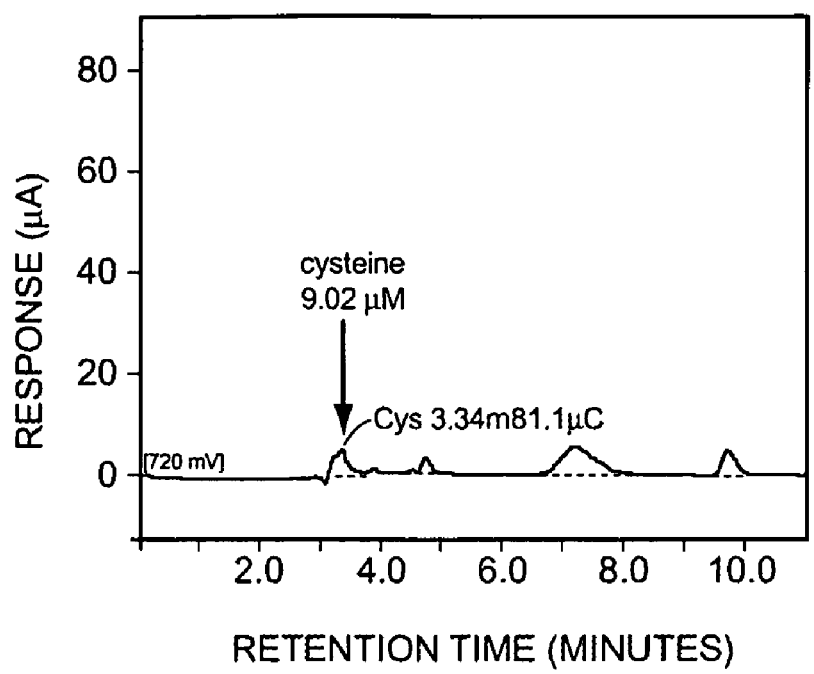
Figure 3D:
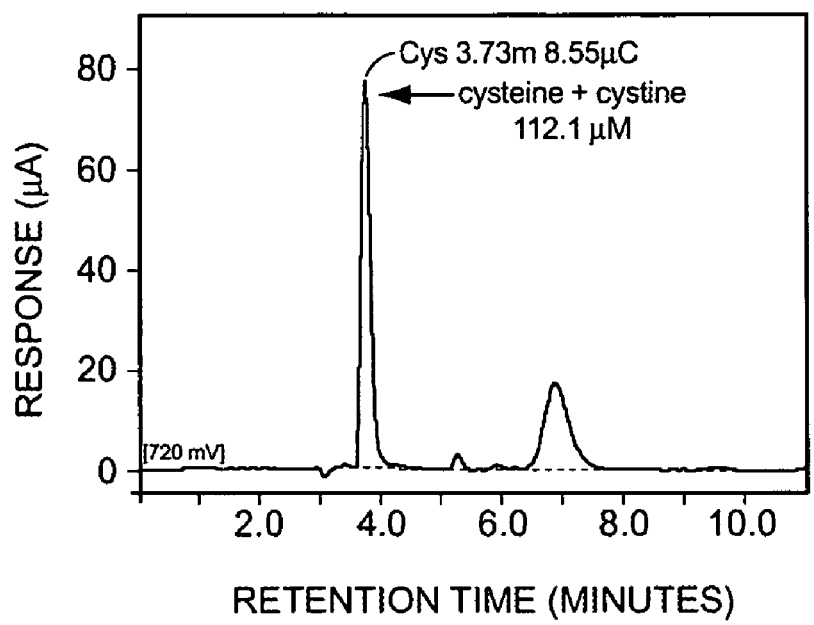

The samples were acidified using 8% m-phosphoric acid and the proteins were precipitated by centrifugation. Resultant extracts were filtered and injected into the HPLC instrument. For detection of cystine (oxidized-form), the samples were first treated with 2-mercaptoethanol for 10 min at room temperature followed by acid extraction with 8% m-phosphoric acid, as described above. HPLC conditions were similar to those of glutathione except for the mobile phase, the composition was 50 mM sodium phosphate (pH 3.0). As shown in FIGS. 3C and D, respectively, this filtered media preparation comprised 10.64 µM cysteine (reduced form) and 112.1 µM cysteine plus cystine.

Collectively these results demonstrate that the conditioned media comprises culture-derived antioxidants. HPLC testing for additional antioxidants, such as ubiquinone, ubiquinol, superoxide dismutase, catalase, glutathione peroxidase, and the like can be performed using the same or similar methodology. Alternatively, antioxidant enzyme activity can be determined using appropriate enzyme assays, as known in the art.

EXAMPLE 7

Effect of Conditioned Media on Collagen Deposition

This example demonstrates the effect of conditioned media on the deposition of extracellular matrix components by fibroblast in three-dimensional cell cultures. Collagen type I pro-peptide (also known as collagen type I telopeptide) was used as an indicator of collagen type I, itself an indicator of extracellular matrix component production. Conditioned media was obtained from the end-term media change in the Dermagraft® process (approximately 2 weeks) and concentrated by ultrafiltration in a concentrator (Amicon, Beverley, Mass.) under nitrogen pressure. When volume of the conditioned media was concentrated to about one-tenth of the original volume, the concentrated conditioned media was collected. Human dermal fibroblasts in DMEM 1 were seeded into wells of a 96-well tissue culture plate at $5 \times 10^3$ cells/well and placed in a 37° C., 5% $CO_2$ incubator for approximately 48 hours. The media was replaced with either DMEM 1 or DMEM 1 supplemented with 10% concentrated conditioned media so that the final concentration of the conditioned media was approximately 1×. The plate was returned to the incubator for approximately 24 hours. The supernatant was collected from each well and tested for the presence of collagen type I pro-peptide using a commercially available collagen type I pro-peptide ELISA according to the manufacturer's instructions (Takara Biomedicals, Japan).

Figure 4:
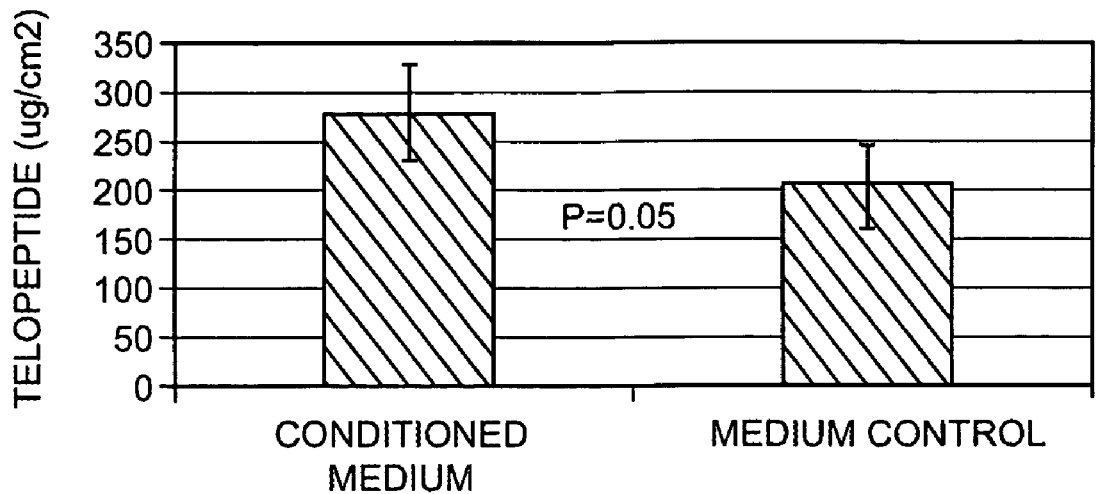
FIG. 4 graphically depicts the effects of control (pre-conditioned) medium and conditioned medium on the collagen deposition by cultured fibroblasts.

As shown in FIG. 4, in this experiment a statistically significant (p=0.05) increase in collagen deposition was observed in cultures maintained in conditioned medium compared to cultures maintained in the pre-conditioned medium. The skilled artisan will appreciate that enhanced in vivo deposition of extracellular matrix components such as collagen would be important for, among other things, the topical treatment of wrinkles and contour defects.

EXAMPLE 8

Conditioned Serum-free or Non-human Animal Product-free Media

This prophetic example illustrates the adaptation of human dermal fibroblast cultures grown in an exemplary serum-containing pre-conditioned DMEM media to pre-conditioned UltraCULTURE™ serum-free media using conventional technology. See, e.g., BioWhittaker 1999/2000 Catalog at pages 42–45. UltraCULTURE™ (BioWhittaker Cat. No. 12-725F) media is supplemented with L-glutamine (Cat. No.17-605) according to the manufacturer's instructions (pre-conditioned UltraCULTURE™ serum-free media).

Monolayer cultures of human dermal fibroblasts are prepared as described in Example 1 above, using pre-conditioned DMEM cell culture media (high-glucose Dulbecco's Modified Eagle's Media (DMEM; GibcoBRL, Grand Island, N.Y.) supplemented with 10% bovine calf serum (Hyclone Laboratories, Logan, Utah), nonessential amino acids (GibcoBRL), and 100 U/ml penecillin-streptomycin-250 ng/ml amphoterecin B (GibcoBRL). The cells are passaged, and split 1:2 using pre-conditioned UltraCULTURE™ serum-free media as the diluent. The cells are plated and incubated in a 37° C., 5% $CO_2$ incubator until maximum cell density is achieved, feeding with pre-conditioned UltraCULTURE™ serum-free media as necessary.

If the cells do not show at least 85% viability, they are passaged at a 1:2 ratio using pre-conditioned UltraCULTURE™ serum-free media supplemented with 0.5% bovine calf serum (HyClone Laboratories) for one passage. For each successive passage the amount of calf serum is decreased by 0.1% so that after five passages, the pre-conditioned UltraCULTURE™ serum-free media contains no serum. At this point the fibroblasts can be propagated in three-dimensional culture, as described in Examples 2 or 3, with the exception that the cells are maintained in pre-conditioned UltraCULTURE™ serum-free media, supplemented with ascorbic acid as appropriate. Conditioned serum-free media is collected at suitable intervals.

If the fibroblast monolayer culture does not successfully adapt to growth in pre-conditioned UltraCULTURE™ serum-free media, an alternate weaning process is used. Cells are passaged as described, centrifuged for 5 minutes at 350×g and resuspended in pre-conditioned UltraCULTURE™ serum-free media containing 5% bovine calf serum (Hyclone), split 1:2 and replated. At the next passage, the cell pellet is resuspended in pre-conditioned UltraCULTURE™ serum-free media containing 2% calf serum, split and plated, as described. On the next five passages, the pellet is resuspended and plated in pre-conditioned UltraCULTURE™ serum-free media containing 2%, then 1%, then 0.5%, then 0.1%, and finally 0% calf serum. At this point the fibroblasts can be propagated in three-dimensional culture, as described in Examples 2 or 3, with the exception that the cells are maintained in pre-conditioned UltraCULTURE™ serum-free media. Conditioned media is collected as appropriate.

UltraCULTURE™ serum-free media was selected for this prophetic example because, among other things, it is a DMEM-based medium and has been shown to support the growth of a number of human cell lines, including the HuS-1* AT skin cell line. See BioWhittaker 1999/2000 catalog at pages 46–47. The skilled artisan will appreciate, however, that a number of serum-free and animal product-free media are also reasonably likely to support the growth of various human cells and that such media can be routinely evaluated without undue experimentation.

While this prophetic example describes the adaptation of human dermal fibroblasts grown in an exemplary pre-conditioned DMEM cell culture medium to an exemplary pre-conditioned serum-free cell culture media, the skilled artisan will understand that the same procedure could be used to adapt a variety of cultured cells, in either serum-containing or serum-free medium, to growth in pre-conditioned animal product-free medium. Following adaptation to growth in animal product-free medium, such cells can be propagated in three-dimensional culture, as described, and conditioned non-human animal product-free medium collected as appropriate.

EXAMPLE 9

Enhancement of Expression of KGF

Figure 5:
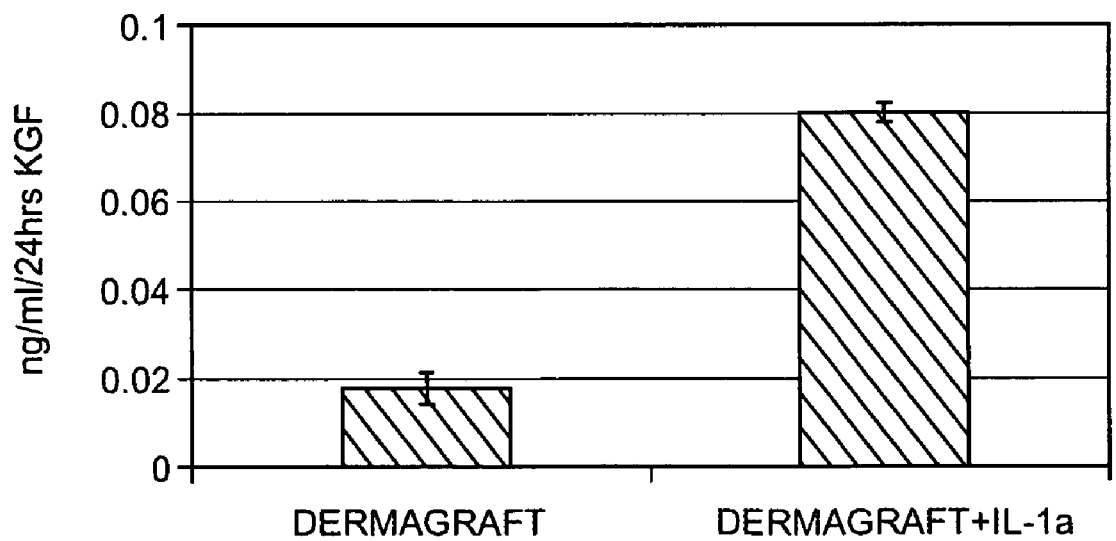
FIG. 5 graphically depicts the enhancement, or up-regulation, of KGF secretion by three-dimensional human dermal fibroblast cultures (Dermagraft®) in the presence of IL-1α compared to parallel cultures in the absence of IL-1α.

This example demonstrates the induction of keratinocyte growth factor (KGF) secretion by human dermal fibroblasts in a three-dimensional culture under appropriate conditions. Pieces of Dermagraft®, approximately 11 mm×11 mm, were placed in wells of a 24-well tissue culture plate. The cells were maintained in a 37° C., 5% $CO_2$ incubator and fed either DMEM2 or DMEM2 supplemented with interleukin-1-alpha (IL-1α) at a concentration of 1 ng/ml. Conditioned media was collected every 24 hours. The concentration of KGF in the conditioned media was determined using a human KGF immunoassay (Quantikine, R & D Systems) according to the manufacturer's instructions. The results, shown in FIG. 5, demonstrate that the level of KGF present in the conditioned media from Dermagraft® samples in the presence of IL-1α is, in this experiment, approximately four times greater than in the absence of IL-1α. Thus, in this experiment, KGF expression by human dermal fibroblasts in three-dimensional culture was enhanced by IL-1α.

EXAMPLE 10

Enhancement of Expression of VEGF

Figure 6:
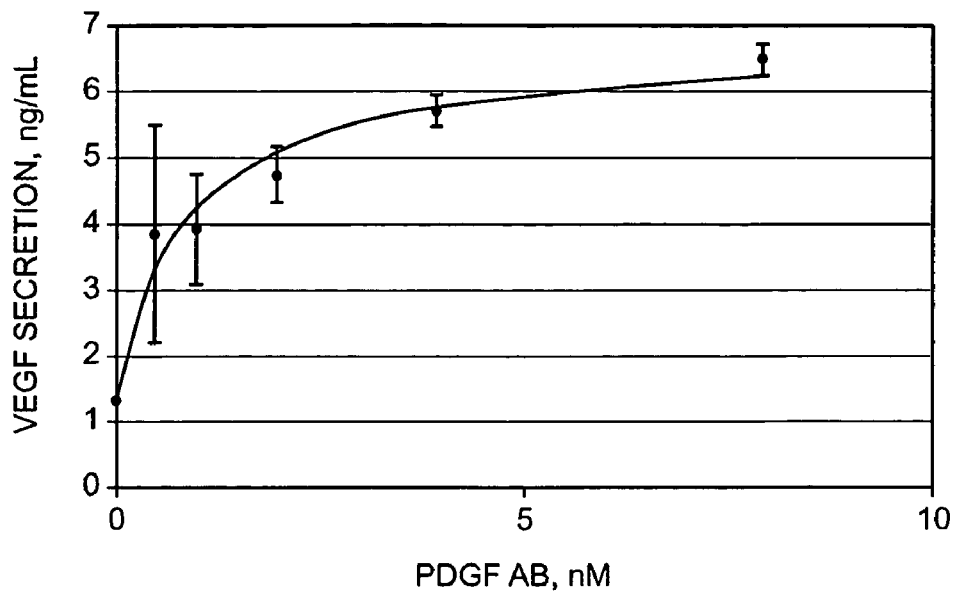
FIG. 6 graphically depicts the enhancement of VEGF secretion in the presence of increasing concentrations of PDGF AB chains.

This example demonstrates that the expression of VEGF by human dermal fibroblasts in three-dimensional cultures may be enhanced under appropriate conditions. Three-dimensional human dermal fibroblast cultures were fed with either pre-conditioned DMEM 2 or pre-conditioned DMEM 2 supplemented with 0.5, 1, 2, 4, or 8 nM PDGF AB (combined A chain and B chain). After incubation for 48 hours at 37° C., the conditioned cell culture media was removed and typically tested the day of collection. The quantity of VEGF present in the six conditioned media samples (0, 0.5, 1, 2, 4, and 8 nM PDGF) was measured using the Quantikine human VEGF immunoassay kit (Cat. No. DVE00, R & D Systems) according to the manufacturer's instructions. As shown in FIG. 6, the presence of increasing quantities of PDGF in the pre-conditioned media resulted in an increase in VEGF secretion. In this experiment, three-dimensional cultures in the absence of exogenous PDGF produced approximately 1.3 ng/ml of VEGF, while parallel cultures in media comprising up to 8 nM PDGF, produced up to approximately 6 ng/ml of VEGF. These results demonstrate that the level of VEGF secretion can be enhanced in the presence nanomolar or even subnanomolar concentrations of PDGF.

EXAMPLE 11

Comparison of VEGF Secretion by Culture Conditions

To evaluate the effect of culture conditions on VEGF secretion, human dermal fibroblasts were grown in parallel in: a) monolayer culture, b) three-dimensional collagen gel culture, c) three-dimensional contracted collagen gel culture, and d) on a three-dimensional scaffold. For monolayer cultures, $3 \times 10^6$ passage 8 human dermal fibroblasts were seeded in 100 mm tissue culture dishes. The three-dimensional scaffold comprised a 5.5×5.5 cm silastic-backed knitted nylon mesh (Biobrane®, Dow Hickum) that was pre-soaked in fetal bovine serum. Following pretreatment, the scaffold was placed in a 100 mm tissue culture dish and $3 \times 10^6$ passage 8 human dermal fibroblasts were seeded onto the scaffold ("scaffold-based"). The dishes were placed in 37° C., 5% $CO_2$ incubator and the cells were fed DMEM supplemented with 10% bovine calf serum, 2 mM L-glutamine, 50 μg/ml ascorbate-phosphate, and 10 U/ml penicillin-streptomycin.

The two collagen gel cultures were prepared by suspending $3 \times 10^6$ passage 8 human dermal fibroblasts in 10 ml Vitrogen (Collagen Corp.) and the suspension was poured into either conventional 100 mm tissue culture dishes ("stressed gel") or, for the contracted collagen gel culture, 100 mm non-treated culture dishes (Costar) ("contracting gel"). The dishes were placed in 37° C., 5% $CO_2$ incubator and the cells were fed DMEM supplemented with 10% bovine calf serum, 2 mM L-glutamine, 50 μg/ml ascorbate-phosphate, and 10 U/ml penicillin-streptomycin. The collagen rapidly polymerized in the incubator with the fibroblasts in suspension. The collagen polymer in the conventional tissue culture dishes remained in contact with the sides of the dishes. In contrast, the collagen polymer in the non-treated culture dishes contracted, causing the polymer to pull away from the sides of the culture dish.

Figure 7:
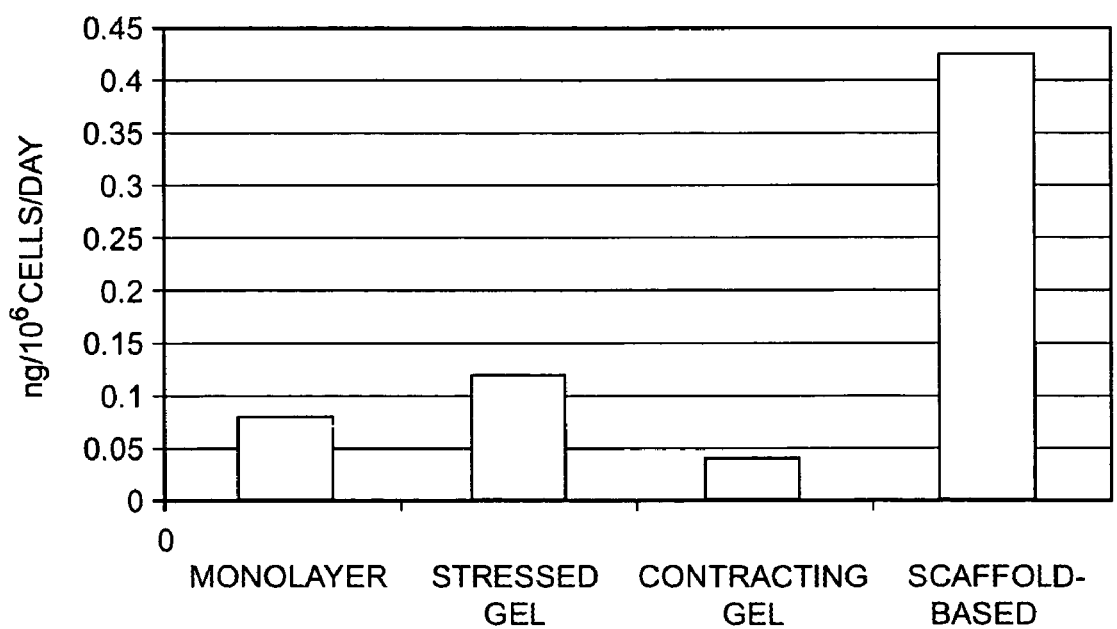
FIG. 7 provides a graphic comparison of the levels of VEGF secretion by fibroblast monolayer cultures, fibroblast stressed collagen gel three-dimensional cultures, fibroblast contracted collagen gel three-dimensional cultures, and fibroblast scaffold-based three-dimensional cultures.

The cultures were fed with fresh pre-conditioned media every three to four days. Conditioned media was collected from each of the four culture systems after approximately two weeks and analyzed. The amount of human VEGF produced by each of the four cultures was determined using the Quantikine human VEGF immunoassay (R & D Systems) following the manufacturer's instructions. The results were standardized based on the nanograms of VEGF secreted per $10^6$ cells per day. As shown in FIG. 7, in this experiment, the monolayer culture secreted less than 1 ng VEGF/$10^6$ cells/day, and the stressed collagen gel and contracting collagen cultures secreted approximately 1.5 ng VEGF/$10^6$ cells/day and 0.5 ng VEGF/$10^6$ cells/day, respectively. The scaffold-based culture, by comparison, secreted more than 4.0 ng VEGF/$10^6$ cells/day.

EXAMPLE 12

Conditioned Media Safety Study

To evaluate the safety of the conditioned media for use in cosmeceutical compositions, nutrient solution was applied topically to human patients and the appearance of cutaneous irritation after successive and continuous exposure under normal and abraided conditions was determined.

Nutrient solution was tested for primary and cumulative irritation on normal, human, adult, forearm skin using standard cosmetic safety protocols. Two hundred microliters of either control or nutrient solution was applied to a 3.8 $cm^2$ occluded patch (Webril non-woven cotton pad) on the upper forearm. The patch was held in place with a 3M® hypoallergenic tape. The primary irritation study involved 15 subjects (13 females and two males, 28–77 years of age). Nutrient solution was applied in two 24 hour intervals to the occluded patches on normal and abraided (tape stripped five times using Transpore tape to remove outer layers of the stratum corneum) skin on the subject's upper forearm of. The cumulative irritation study involved 31 subjects (21 females and 10 males, 20–65 years of age). One subject withdrew due to tape irritation and one due to personal reasons. Twenty-nine subjects, 19 females and 10 males completed the study. Nutrient solution was on the upper forearm in 14, consecutive, 24 hour applications. Gross observations were graded for glazing, peeling, scabbing, fissuring, hyperpigmentation and hypopigmentation. Irritation was scored visually using a 5 point scale and graded numerically for erythema, edema, papules, vesicles, bulla reactions, weeping, spreading, and induration. As determined by licensed health care professionals, no adverse events were induced by the nutrient solution or control in these studies.

EXAMPLE 13

Conditioned Media Efficacy Study

To assess the cosmeceutical effect of nutrient solution on the histology of normal and photodamaged human skin, an occlusive patch test was conducted, essentially as described in Example 12. An occluded patch with nutrient solution was applied daily to the forearm of each of 6 female subjects (37–46 years of age) from Monday through Friday with examination on Saturday. Three subjects received patches for 5 days and 3 subjects for 12 days. Punch biopsies (2 mm) were taken on the day after the last patch. The biopsies were fixed in 10% formalin, embedded in paraffin and 4 micron sections cut and stained with H&E, tri-chrome for collagen, Verhoeff Van Grieson stain for elastin. Irritation was scored as in the safety studies. No significant irritation was observed in the subjects. Upon histological examination of the stained sections at a magnification of 100× and 250×, no difference in cell architecture was seen between the nutrient solution and the control. A progressive increase in epidermal thickening and fibroblast and nuclei was seen from 0 to 2 to 4 weeks. By week 4, the average epidermal thickness increased by 22% and dermal fibroblast nuclei increased by 38%.

EXAMPLE 14

Clinical Evaluation of Three-Dimensional Culture (Dermagraft®) Conditioned Media Conditioned cell culture media was obtained from a preparation of Dermagraft® (Advanced Tissue Sciences, La Jolla, Calif.), a tissue-engineered product comprising human dermal fibroblasts grown on a three-dimensional framework. The conditioned media was applied twice daily to the forearms of six human subjects. Biopsies were obtained at days 0, 14 and 28 of the study and examined histologically using conventional methods. The forearm biopsy material showed an increase in collagen type I (++), collagen type III (+++), hyaluronic acid (+++), and elastin (++) at day 28, compared to biopsy material collected at day 0. A progressive increase in epidermal thickening and fibroblast nuclei was also observed histologically over the four week study interval.

EXAMPLE 15

Generation of Transport-Enhanced Growth Factors

This prophetic example describes the generation of transport-enhanced growth factors using conventional molecular biology techniques. See, e.g., Ausbel et al., Sambrook and Russell, and Sambrook et al. A gene fragment encoding a growth factor, such as any of the growth factors identified on Table 3, is fused with a gene fragment encoding a transport peptide, for example, but not limited to, one of the transport peptide sequences shown in Table 1 (SEQ ID NO:1–SEQ ID NO:19). Typically, the gene fragment encoding the transport peptide is fused upstream of the gene fragment encoding the growth factor, such that the transport peptide is at the amino terminus of the transport-enhanced growth factor. For example, a fused gene fragment is generated using conventional molecular biology techniques, such as by ligating a DNA sequence encoding SEQ ID NO:3 with a DNA sequence encoding VEGF. The nucleotide sequence of VEGF is known in the art. Thus, an exemplary DNA sequence encoding the SEQ ID NO:3 transport peptide: CGUAAAAMCGUCGUCAACGUCGUCGU (SEQ ID NO:20) is ligated to the DNA sequence encoding VEGF. Due to the redundancy of the DNA code, the skilled artisan will understand that many alternate sequences encode the transport peptide and the amino acid sequence of VEGF. For example, one of many alternate sequence encoding the SEQ ID NO:3 transport peptide is CGCAAAAMCGCCGC-CAACGCCGCCGC (SEQ ID NO:21). Thus, the skilled artisan understands that typically, any nucleic acid sequence that encodes the amino, acid sequence of the desired transport peptide can be fused with any nucleic acid sequence that encodes the amino acid sequence of the desired growth factor to yield the transport-enhanced growth factor fused gene fragment.

The transport-enhanced growth factor fused gene fragment is then inserted into an appropriate expression vector for expression in the desired host cell, typically human cells such as fibroblasts, keratinocytes, chondrocytes, smooth muscle cells, and the like, using conventional molecular biology techniques. The expression vector will typically comprise a 5' flanking sequence and other appropriate regulatory elements as well as an enhancer(s), a transcriptional termination element, optionally, a complete intron sequence containing a donor and acceptor splice site, a signal peptide sequence if necessary, a ribosome binding site element, a polyadenylation sequence, and a selectable marker.

The transport-enhanced growth factor expression vector is then used to tranfect, for example, but not limited to, human dermal fibroblasts, using conventional molecular biology techniques such as, for example, calcium phosphate co-precipitation or electroporation. Transformed cells comprising the transport-enhanced growth factor expression vector are selected, using conventional molecular biology techniques, and the cells expanded in monolayer culture. The monolayer cells may then be used to seed three-dimensional cultures, such as those describe above. Media conditioned using such three-dimensional cultures should comprise the desired transport-enhanced growth factor, here transport-enhanced VEGF.

The skilled artisan understands that while this example describes the formation of a transport-enhanced growth factor gene fragment using the HIV-1 Tat transduction domain (SEQ ID NO:3) and VEGF, any number of combinations of nucleic acid sequence encoding desired growth factors can be fused with any number of nucleic acid sequences encoding any of the transport peptides shown in Table 1 to generate a transport-enhanced growth factor gene fragment without undue experimentation.

EXAMPLE 16

Generation of Transport-Enhanced Antioxidants

This prophetic example describes the generation of transport-enhanced antioxidants using conventional molecular biology techniques. See, e.g., Ausbel et al., Sambrook and Russell, and Sambrook et al. A gene fragment encoding an antioxidant is fused with a gene fragment encoding a transport peptide. Typically, the gene fragment encoding the transport peptide is fused upstream of the gene fragment encoding the antioxidant, such that the transport peptide is at or near the amino terminus of the transport-enhanced antioxidant.

For example, a gene fragment encoding an antioxidant, such as glutathione, glutathione peroxidase, glutathione reductase, glutathione disulfide, catalase, superoxide dismutase, alpha-tocopherol, gamma-tocopherol, ubiquinol-9, ubiquinone 9, or ascorbic acid, is fused with a gene fragment encoding a transport peptide, for example, but not limited to, one of the transport peptide sequences shown in Table 1 (SEQ ID NO:1-SEQ ID NO:19). Typically, the gene fragment encoding the transport peptide is fused upstream of the gene fragment encoding the antioxidant, such that the transport peptide is at the amino terminus of the transport-enhanced antioxidant. For example, a fused gene fragment is generated using conventional molecular biology techniques, such as by ligating a DNA sequence encoding SEQ ID NO:18 with a DNA encoding glutathione, the nucleotide sequence of which is readily available in the art. Thus, an exemplary DNA sequence encoding the SEQ ID NO:18 transport peptide: AGAAGAAGMGAAGAAGA (SEQ ID NO:22) is ligated to the DNA sequence encoding glutathione (γ-glutamylcysteinylglycine), for example, CAAUGUGGU (SEQ ID NO:23). Due to the redundancy of the DNA code, the skilled artisan will understand that many alternate sequences encode the transport peptide and the amino acid sequence of glutathione. For example, one of several alternate sequence encoding for glutathione is CAAUGUGGC (SEQ ID NO:24). Thus, the skilled artisan understands that typically, any nucleic acid sequence that encodes the amino acid sequence of the desired transport peptide can be fused with any nucleic acid sequence that encodes the amino acid sequence of the desired antioxidant to yield the transport-enhanced antioxidant fused gene fragment.

The transport-enhanced antioxidant fused gene fragment is then inserted into an appropriate expression vector for expression in the desired host cell, typically human cells such as fibroblasts, keratinocytes, chondrocytes, smooth muscle cells, and the like, using conventional molecular biology techniques. The expression vector will typically comprise a 5' flanking sequence and other appropriate regulatory elements as well as an enhancer(s), a transcriptional termination element, optionally, a complete intron sequence containing a donor and acceptor splice site, a signal peptide sequence if necessary, a ribosome binding site element, a polyadenylation sequence, and a selectable marker.

The transport-enhanced antioxidant expression vector is then used to tranfect, for example, but not limited to, human dermal fibroblasts, using conventional molecular biology techniques such as, for example, calcium phosphate coprecipitation or electroporation. Stably transformed cells comprising the transport-enhanced growth factor expression vector are selected, using conventional molecular biology techniques, and the cells expanded in monolayer culture. The monolayer cells may then be used to seed three-dimensional cultures, such as those describe above. Media conditioned using such three-dimensional cultures should comprise the desired transport-enhanced antioxidant, here transport-enhanced glutathione.

The skilled artisan understands that while this example describes the formation of a transport-enhanced antioxidant gene fragment using the $R_6$ sequence (SEQ ID NO:18) and glutathione, any number of combinations of nucleic acid sequence encoding desired antioxidants can be fused with any number of nucleic acid sequences encoding any of the transport peptides shown in Table 1 to generate a transport-enhanced antioxidant gene fragment without undue experimentation.

Methods such as described in Examples 15 and 16 can also be used to generate transport-enhanced extracellular matrix components, which are also within the scope of the invention.

Although the invention has been described with reference to various applications, methods, and compositions, it will be appreciated that various changes and modifications may be made without departing from the scope of the invention.

What is claimed is:

1. A composition comprising: conditioned cell culture media, or an extract thereof, comprising at least one culture-derived growth factor, wherein the at least one growth factor comprises at least one of vascular endothelial growth factor (VEGF), transforming growth factor beta (TGFβ), hepatocyte growth factor (HGF), keratinocyte growth factor (KGF), interleukin-3 (IL-3), IL-6, and IL-8; at least one culture-derived antioxidant, wherein the at least one antioxidant comprises at least one of glutathione, glutathione peroxidase, glutathione reductase, glutathione disulfide, catalase, superoxide dismutase, alpha-tocopherol, gamma-tocopherol, ubiquinol-9, ubiquinone 9, ascorbic acid, cysteine, and cystine; and at least one culture-derived soluble collagen; and an appropriate carrier, and wherein the cell culture media is conditioned by human fibroblasts in three-dimensional culture.

2. The composition of claim 1, wherein the at least one growth factor comprises a genetically-engineered growth factor.

3. The composition of claim 2, wherein the genetically-engineered growth factor comprises at least one transport-enhanced growth factor.

4. The composition of claim 1, wherein the at least one antioxidant comprises at least one genetically-engineered antioxidant.

5. The composition of claim 4, wherein the at least one genetically-engineered antioxidant comprises at least one transport-enhanced antioxidant.

6. The composition of claim 1, wherein the appropriate carrier is a pharmaceutically-acceptable carrier.

7. The composition of claim 1, wherein the appropriate carrier is a cosmetically-acceptable carrier.

8. The composition of claim 1, wherein the appropriate carrier is a cosmeceutically-acceptable carrier.

9. The composition of claim 1 wherein the three-dimensional culture comprises a framework, a collagen matrix, a gelatin matrix, or a gel matrix.

10. The composition of claim 9, wherein the three-dimensional culture comprises a framework or a contracted collagen gel matrix.

11. The composition of claim 9, wherein the three-dimensional culture comprises a framework.

12. The composition of claim 1, wherein the composition is substantially free from phenol red.

13. The composition of claim 1, wherein the composition is substantially free from components of bovine-origin.

14. The composition of claim 1, wherein the composition is substantially free from non-human animal products.

15. The composition of claim 1, wherein at the least one growth factor comprises a genetically-engineered growth factor.

16. The composition of claim 15, wherein the genetically-engineered growth factor comprises at least one transport-enhanced growth factor.

17. The composition of claim 16, wherein the at least one transport-enhanced growth factor comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19.

18. The composition of claim 1, wherein the at least one antioxidant comprises at least one genetically-engineered antioxidant.

19. The composition of claim 18, wherein the at least one genetically-engineered antioxidant comprises at least one transport-enhanced antioxidant.

20. The composition of claim 19, wherein the at least one transport-enhanced antioxidant comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19.

21. A cosmeceutical composition comprising: cell culture media or an extract thereof, conditioned by incubation with a three-dimensional cell culture, wherein the conditioned media or extract comprises at least one culture-derived growth factor, the at least one growth factor comprising at least one of: vascular endothelial growth factor (VEGF), transforming growth factor beta (TGFIβ), hepatocyte growth factor (HGF), keratinocyte growth factor (KGF), interleukin-3 (IL-3), IL-6, and IL-8; and at least one culture-derived antioxidant, the at least one antioxidant comprising at least one of: glutathione, glutathione peroxidase, glutathione reductase, glutathione disulfide, catalase, superoxide dismutase, alpha-tocopherol, gamma-tocopherol, ubiquinol-9, ubiquinone 9, ascorbic acid, cysteine, and cystine; and a cosmeceutically-acceptable carrier, and wherein the cell culture media is conditioned by human fibroblasts in three-dimensional culture.

22. The composition of claim 21, wherein at the least one growth factor comprises a genetically-engineered growth factor.

23. The composition of claim 22, wherein the genetically-engineered growth factor comprises at least one transport-enhanced growth factor.

24. The composition of claim 23, wherein the at least one transport-enhanced growth factor comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19.

25. The composition of claim 21, wherein the at least one antioxidant comprises at least one genetically-engineered antioxidant.

26. The composition of claim 25, wherein the at least one genetically-engineered antioxidant comprises at least one transport-enhanced antioxidant.

27. The composition of claim 26, wherein the at least one transport-enhanced antioxidant comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19.

28. The composition of claim 21, wherein said at least one growth factor comprises KGF.

29. The composition of claim 28, wherein the three-dimensional fibroblast culture is treated with an amount of IL-1α a sufficient to enhance the expression of KGF.

30. The composition of claim 21, wherein the three-dimensional fibroblast culture is treated with an amount of PDGF sufficient to enhance the expression of VEGF.

31. The composition of claim 21, wherein the composition is substantially free from phenol red.

32. The composition of claim 21, wherein the composition is substantially free from components of bovine-origin.

33. The composition of claim 21, wherein the composition is substantially free from non-human animal products.

34. The composition of claim 21, wherein the three-dimensional culture comprises a framework, a collagen matrix, a gelatin matrix, or a gel matrix.

35. The composition of claim 34, wherein the three-dimensional culture comprises a framework or a contracted collagen gel matrix.

36. The composition of claim 35, wherein the three-dimensional culture comprises a framework.

37. The composition of claim 21, further comprising at least one culture-derived soluble collagen.

38. A method for preparing a cosmeceutical composition comprising: combining a pre-conditioned medium with a thee-dimensional cell culture under appropriate conditions to generate a conditioned medium comprising at least one culture-derived growth factor, the at least one growth factor comprising at least one of: vascular endothelial growth factor (VEGF), transforming growth factor beta (TGFβ), hepatocyte growth factor (HGF), keratinocyte growth factor (KGF), interleukin-3 (IL-3), IL-6, and IL-8; and at least one culture-derived antioxidant, the at least one antioxidant comprising at least one of: glutathione, glutathione peroxidase, glutathione reductase, glutathione disulfide, catalase, superoxide dismutase, alpha-tocopherol, gamma-tocopherol, ubiquinol-9, ubiquinone 9, ascorbic acid, cysteine, and cystine; and combining the conditioned medium with a cosmeceutically-acceptable carrier to form a cosmeceutical composition, wherein the cell culture media is conditioned by human fibroblasts in three-dimensional culture, and wherein the at least one growth factor comprises at least one genetically-engineered transport-enhanced growth factor and/or and the at least one antioxidant comprises at least one genetically-engineered transport-enhanced antioxidant.

39. A method for preparing a composition comprising: combining a pre-conditioned medium with a three-dimensional cell culture under appropriate conditions to generate a conditioned medium comprising at least one culture-derived growth factor, the at least one growth factor comprising at least one of: vascular endothelial growth factor (VEGF), transforming growth factor beta (TGFβ), hepatocyte growth factor (HGF), keratinocyte growth factor (KGF), interleukin-3 (IL-3), IL-6, and IL-8; and at least one culture-derived antioxidant, the at least one antioxidant comprising at least one of: glutathione, glutathione peroxidase, glutathione reductase, glutathione disulfide, catalase, superoxide dismutase, alpha-tocopherol, gamma-tocopherol, ubiquinol-9, ubiquinone 9, ascorbic acid, cysteine, and cystine; and combining the conditioned medium with an acceptable carrier to form a composition, wherein the cell culture media is conditioned by human fibroblasts in three-dimensional culture, and wherein the at least one growth factor comprises at least one genetically-engineered transport-enhanced growth factor and/or and the at least one antioxidant comprises at least one genetically-engineered transport-enhanced antioxidant.

40. The method of claim 39, wherein the acceptable carrier is a pharmaceutically-acceptable carrier.

41. The method of claims 38 or 39, wherein the three-dimensional culture comprises a framework, a collagen matrix, a gelatin matrix, or a gel matrix.

42. The method of claim 41, wherein the three-dimensional culture comprises a framework or a contracted collagen gel matrix.

43. The method of claims 38 or 39, wherein the composition is substantially-free from phenol red.

44. The method of claims 38 or 39, wherein the composition is substantially-free from components of bovine-origin.

45. The method of claims 38 or 39, wherein the composition is substantially-free from non-human animal products.

46. The method of claim 38 or 39, wherein the at least one transport-enhanced growth factor comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19.

47. The method of claim 38 or 39, wherein the at least one transport-enhanced antioxidant comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19.

48. The method of claims 38 or 39, wherein an extract of the conditioned medium is combined with the carrier to form the composition.

* * * * *

US007160726C1

(12) EX PARTE REEXAMINATION CERTIFICATE (7126th)
United States Patent
Mansbridge

(10) Number: US 7,160,726 C1
(45) Certificate Issued: *Oct. 27, 2009

(54) COMPOSITIONS COMPRISING CONDITIONED CELL CULTURE MEDIA AND USES THEREOF

(75) Inventor: Jonathan N. Mansbridge, La Jolla, CA (US)

(73) Assignee: Skinmedia, Inc., Carlsbad, CA (US)

Reexamination Request:
No. 90/008,852, Sep. 20, 2007

Reexamination Certificate for:
| | |
|---|---|
| Patent No.: | 7,160,726 |
| Issued: | Jan. 9, 2007 |
| Appl. No.: | 10/165,860 |
| Filed: | Jun. 7, 2002 |

(*) Notice: This patent is subject to a terminal disclaimer.

Related U.S. Application Data

(60) Provisional application No. 60/297,177, filed on Jun. 7, 2001.

(51) Int. Cl.
*C12N 5/00* (2006.01)
*C12N 5/08* (2006.01)

(52) U.S. Cl. .................. 435/391; 424/198.1; 514/2; 435/325; 435/366; 435/371; 435/395

(58) Field of Classification Search .................. None
See application file for complete search history.

(56) References Cited

U.S. PATENT DOCUMENTS

| | | | |
|---|---|---|---|
| 4,458,678 A | 7/1984 | Yannas et al. |
| 4,485,096 A | 11/1984 | Bell et al. |
| 4,861,714 A | 8/1989 | Dean, Jr. et al. |
| 4,911,720 A | 3/1990 | Collier |
| 4,963,489 A | 10/1990 | Naughton et al. |
| 5,008,240 A | 4/1991 | Bentz et al. |
| 5,032,508 A | 7/1991 | Naughton et al. |
| 5,043,156 A | 8/1991 | Matsumoto et al. |
| 5,091,173 A | 2/1992 | Buultjens et al. |
| 5,229,493 A | 7/1993 | Folkman et al. |
| 5,266,480 A | 11/1993 | Naughton et al. |
| 5,443,950 A | 8/1995 | Naughton et al. |
| 5,460,939 A | 10/1995 | Hansbrough et al. |
| 5,474,931 A | 12/1995 | DiSorbo et al. |
| 5,478,739 A | 12/1995 | Slivka et al. |
| 5,516,532 A | 5/1996 | Atala et al. |
| 5,516,681 A | 5/1996 | Naughton et al. |
| 5,565,347 A | 10/1996 | Fillatti et al. |
| 5,618,544 A | 4/1997 | Brown |
| 5,654,381 A | 8/1997 | Hrkach et al. |
| 5,681,748 A | 10/1997 | DiSorbo et al. |
| 5,709,854 A | 1/1998 | Griffith-Cima |
| 5,736,372 A | 4/1998 | Vacanti et al. |
| 5,759,830 A | 6/1998 | Vacanti et al. |
| 5,763,267 A | 6/1998 | Kurjan et al. |
| 5,770,193 A | 6/1998 | Vacanti et al. |
| 5,830,709 A | 11/1998 | Naughton |
| 5,843,766 A | 12/1998 | Applegate et al. |
| 5,855,918 A | 1/1999 | Mrsny et al. |
| 5,888,551 A | 3/1999 | Jimenez et al. |
| 5,900,245 A | 5/1999 | Sawhney et al. |
| 5,902,741 A | 5/1999 | Purchio et al. |
| 5,935,849 A | 8/1999 | Schinstine et al. |
| 5,965,125 A | 10/1999 | Mineau-Hanschke |
| 6,080,724 A | 6/2000 | Chassaing et al. |
| 6,291,240 B1 | 9/2001 | Mansbridge |
| 6,372,494 B1 | 4/2002 | Naughton |
| 7,118,746 B1 | 10/2006 | Naughton et al. |
| 7,160,726 B2 | 1/2007 | Mansbridge |
| 2004/0142861 A1 | 7/2004 | Mansbridge |
| 2007/0077232 A1 | 4/2007 | Naughton et al. |
| 2007/0218549 A1 | 9/2007 | Mansbridge |

FOREIGN PATENT DOCUMENTS

| | | |
|---|---|---|
| AU | 772829 | 5/2005 |
| AU | 20022345603 | 1/2007 |
| CN | 1198628 C | 4/2005 |
| EP | 0476983 | 9/1991 |
| EP | 1178812 B2 | 12/2005 |
| JP | 2004-534049 A | 11/2004 |
| NZ | 515476 | 5/2000 |
| RU | 2054924 | 2/1996 |
| RU | 2063743 | 7/1996 |
| RU | 2123837 | 12/1998 |
| RU | 2141814 | 11/1999 |
| RU | 2142783 | 12/1999 |
| RU | 2280459 | 7/2006 |
| SG | 106171 | 6/2006 |
| WO | WO-89/11529 | 11/1989 |
| WO | WO-91/16010 | 10/1991 |
| WO | WO-93/04164 | 3/1993 |
| WO | WO-93/17669 | 9/1993 |
| WO | WO-94/20133 | 9/1994 |
| WO | WO-94/25080 | 11/1994 |

(Continued)

OTHER PUBLICATIONS

US 5,785,954, 7/1998, Naughton et al. (withdrawn)
Bell, E. et al., "Living Tissue Formed in vitro and Accepted as Skin–Equivalent Tissue of Full Thickness," Science 211:1052–1054 (1981).
Doillon, C.J. et al., "Fibroblast–Collagen Sponge Interactions and the Spatial Deposition of Newly Synthesized Collagen Fibers in vitro and in vivo," Scanning Electron Microscopy 111:1313–1320 (1984).

(Continued)

*Primary Examiner*—Padmashri Ponnaluri

(57) ABSTRACT

The invention relates to compositions comprising cell culture medium conditioned by cells grown in three-dimensional culture. The cells used to condition the medium may be genetically modified to alter the concentration of growth factors and antioxidants in the medium. The conditioned cell medium (conditioned medium) may be used for at least one of cosmetic applications, cosmeceutical applications, and pharmaceutical applications, among other things. The invention also relates to proteins comprising a heterologous sequence that enhances cell penetration. The invention also relates to cells comprising DNA encoding such proteins. Methods for preparing the inventive compounds are also provided.

FOREIGN PATENT DOCUMENTS

| WO | WO-96/18726 | 6/1996 |
|---|---|---|
| WO | WO-96/39101 | 12/1996 |
| WO | WO-96/40174 | 12/1996 |
| WO | WO-97/21442 | 6/1997 |
| WO | WO-98/21312 | 11/1997 |
| WO | WO-98/07832 A1 | 2/1998 |
| WO | WO-98/16642 A1 | 4/1998 |
| WO | WO-99/11809 A1 | 3/1999 |
| WO | WO-99/59615 A1 | 11/1999 |
| WO | WO-00/29427 A2 | 5/2000 |
| WO | WO-00/46349 | 8/2000 |
| WO | WO-00/69449 A2 | 11/2000 |
| WO | WO 01/14527 A1 * | 3/2001 |
| WO | WO 2001-14527 A1 | 3/2001 |
| ZA | 2001/9381 | 1/2003 |

OTHER PUBLICATIONS

Fontaine, A.R. and Hall, B.D., "Biocompatibility of echinoderm skeleton with mammalian cells in vitro: Preliminary evidence," J. Biomed. Materials Res. 15:61–71 (1981).

Gibson, G.J. et al., "Synthesis of a Low Molecular Weight Collagen by Chondrocytes from the Presumptive Calcification Region of the Embryonic Chick Sterna: The Influence of Culture with Collagen Cells," J. Cell Biology 99:208–216 (1984).

Jiang, W.G. and Harding, K.G., "Enhancement of wound tissue expansion and agiogenesis by matrix–embedded fibroblast (Dermagraft), a role of hepatocyte growth factor/ scatter factor," Intl. J. Mol. Medicine 2:203–210 (1998).

Mansbridge, J. et al. "Three–Dimensional Fibroblast Culture Implant for the Treatment of Diabetic Foot Ulcers: Metabolic Activity and Therapeutic Range," Tissue Engineering 4(4):403–414 (1998).

Matsuzaki, T. and Yoshizato, K., "Role of hair papilla cells on induction and regeneration processes of hair follicles," Wound Repair & Regeneration 6(6):524–530 (1998).

Mikayama et al., "Molecular cloning and functional expression of a cDNA encoding glycosylation–inhibiting factor," PNAS USA 90:10056–10060 (1993).

Voet, D. and Voet, J., Biochemistry , John Wiley & Sons, Inc. 1990, pp. 126–128 and 228–234.

Barka, T. et al., "Transduction of TAT–HA–β–galactosidase Fusion Protein into Salivary Gland–derived Cells and Organ Cultures of the Developing Gland, and into Rat Submandibular Gland in Vivo," J. Histochem. Cytochem. 48(11):1453–1460 (2000).

Barnes, D. and Sato, G., "Methods for Growth of Cultured Cells in Serum–Free Medium," Anal. Biochem. 102:255 (1980).

Barnes, D. "Serum–Free Animal Cell Culture," Biotechniques 5(6):534–542 (1987).

Boudreau, N.J. and Jones, P.L., "Extracellular matrix and integrin signalling: the shape of things to come," Biochem. J. 339:481–488 (1999).

Derossi, D. et al., "Cell Internalization of the Third Helix of the Antennapedia Homeodomain Is Receptor–Independant," J. Biol. Chem. 271(30):18188–18193 (1996).

Engels, J.W. and Uhlmann, E., Gene Synthesis, Angew. Chem. Intl. Ed. 28:716–734 (1989).

Fawell, S. et al., "Tat–mediated delivery of heterologous proteins info cells," PNAS 91:664–668 (1994).

Futaki et al., "Arginine–rich Peptides: An Abundant Source of Membrane–Permeable Peptides Having Potential as Carriers for Intracellular Protein Delivery," J. Biol. Chem. 276:5836–5840 (2001).

Geiger, B. et al., "Transmembrane Extracellular Matrix–Cytoskeleton Crosstalk," Nature Reviews Molecular Cell Biol. 2:793–803 (2001).

Kohen, R. and Gati, I., "Skin low molecular weight antioxidants and their role in aging and in oxidative stress," Toxicology 148:149–157 (2000).

Kohen, R., "Skin antioxidants: their role in aging and in oxidative stress–New approaches for their evaluation," Biomed. Pharmacother. 53:181–192 (1999).

Kohen, R.et al., "Overall Low Molecular Weight Antioxidant Activity of Biological Fluids and Tissues by Cyclic Voltammetry," Methods of Enymol. 300:285–290 (1999).

Kwon et al., "Transduction of Cu,Zn–superoxide dismutase mediated by an HIV–1 Tat protein basic domain into mammalian cells," FEBS Ltrs. 485:163–167 (2000).

Life Technologies, Gibco BRL Products and Reference Guide 1997/1998 catalog, Chapter 1 and 8, especially pp. 1–51.

Miyachi, Y., "Photoaging from an oxidative standpoint," Dermatol. Sci. 9:79–86 (1995).

Naughton, G. "Dermal Equivalents," pp. 891–902, in Principles of Tissue Engineering, $2^{nd}$ ed., Lanza et al., eds., Academic Press, 2000.

Pachence, J.M. and Kohn, J., "Biodegradable Polymers", pp. 263–277, in Principles of Tissue Engineering, $2^{nd}$ ed., Lanza et al. eds. Academic Press, 2000.

Parenteau, N. "The First tissue–Engineered Products," Scientific American 280:83–84 (1999).

Pinney, E. et al., "Human Three–Dimensional Fibroblast Cultures Express Angionenic Activity," J. Cell. Physiol. 183(1):74–82 (2009).

Pinney, E. et al., "Wound Healing Potential of Dermagraft® Conditioned Medium," J. Investigative Dermatology 114(4):828 (2000).

Pooga, M. et al., "Cell penetration by Transportan," FASEB J. 12:67–77 (1998).

Roy et al., "Simultaneous Detection of Tocopherols and Tocotrienols in Biological Samples Using HPLC–Coulometric Electrode Array," Meth. Enzymol. 2001 (in press) need citation.

Royall, J.A. and Ischiropoulos, H., "Evaluation of 2',7'–Dichlorofluorescin and Dihydrorhodamine 123 as Fluorescent Probes for Intracellular $H_2O_2$ in Cultured Endothelial Cells," Arch. Biochem. Biophys. 302:348–355 (1993).

Schwarze, S. et al., "Protein transduction: unrestricted delivery into all cells?" Trends in Cell Biology 10:290–295 (2000).

Sen, C. et al., "Molecular basis of vitamin E action. Tocotrienol potently inhibits glutamate–induced pp60(c–Src) kinase activation and death of HT4 neuronal cells," J. Biol. Chem. 75(17):13049–13055 (2000).

Steffen, W., "Tat–mediated delivery of Antibodies into Cultured Cells," Methods in Mol. Biol. 161:141–148 (2001).

Stephens, D.J. and Pepperkok, R., "The many ways to cross the plasma membrane," PNAS 98(8):4295–4298 (2001) www.pnas.org.cgi/doi/pnas.081065198.

Stohs, S.J., "The Role of Free Radicals in Toxicity and Disease," J. Basic Clin. Physio. Pharmacol. 6:206–228 (1995).

Vives, E. et al., "A Truncated HIV–1 Tat Protein Basic Domain Rapidly Translocates through the Plasma Membrane and Accumulates in the Cell Nucleus," J. Biol. Chem. 272:16010–16017 (1997).

PCT/US02/18057 WO Search Report dated Oct. 7, 2002.

Bell, E. et al., "Production of a tissue–like structure by contraction of collagen lattices by human fibroblasts of different proliferative potential in vitro," PNAS USA 76(3):1274–1278 (1979).

Deuel, T.F., "Growth Factors" in *Principles of Tissue Engineering,* Lanza et al. (eds.), Academic Press, pp. 193–206.

Flax, J.D. et al., "Engraftable human netural stem cells respond to developmental cues, replace neurons, and express foreign genes," Nat. Biotechnol. 16(11):1033–139 (1998).

Folkman, J. and Haudenschild, "Angiogenesis in vitro," Nature 288(5791):551–556 (1980).

Freshney, R.I., "Culture of specific cell types," in *Culture of Animal Cells. A Manual of Basic Technique,* 2$^{nd}$ Ed., A.R. Liss, Inc., New York, Ch. 20, pp. 257–288.

Frisen, J. et al., "Central nervous system stem cells in the embryo and adult," Cell Mol. Life Sci. 54(9):935–945 (1998).

Goey, H. et al., "Inhibition of early murine hemopoietic progenitor cell proliferation after in vivo locoregional administration of transforming growth factor–beta 1," J. Immunol. 143(3):877–880 (1989).

Gonzalez–Rubio, M. et al., "Oxidative stress induces tyrosine phosphorylation of PDGF alpha–and–beta–receptors and pp60c–src in mesangial cells," Kidney Int. 50(1):164–173 (1996).

Green and Thomas, "Pattern formation by cultured human epidermal cells: development of curved ridges resembling dermatoglgphs," Science 200(4348):1385–1388 (1978).

Keller and Snodgrass, "Human embronic stem cells: the future is now," Nat. Med. 5(2):151–152 (1999).

Kielty et al., Collagen: the collagen family: structure, assembly and organization in the extracellular matrix, in *Connective Tissue and its Heritable Disorders: Molecular, Genetic and Medical Aspects,* Rocye and steinmann (eds.), Wiley–Liss, Inc., New York, 1993, pp. 103–147.

Kruse and Miedema, "Production and characterization of multiple–layered populations of animal cells," J. Cell Biol. 27(2):273–279 (1965).

Matsuda, T. et al., "Photoinduced prevention of tissue adhesion," ASAIO J. 38(3):M154–M157 (1992).

Neeman, M. et al., "Regulation of angiogenesis by hypoxic stress: from solid tumours to the ovarian follicle," Int. J. Exp. Pathol. 78(2):57–70 (1997).

Noda and Camilliere, "In vivo stimulation of bone formation by transforming growth factor–beta," Endocrinology 124(6):2991–2994 (1989).

Pierce, G.F. et al., "In vivo incisional wound healing sugmented by platelet–derived growth factor and recombinant c–sis gene homodimeric proteins," J. exp. Med. 167(3):974–987 (1988).

Pietenpol, J.A. et al., "Transforming growth factor beta 1 suppression of c–myc gene transcription: role in inhibition of keratinocyte proliferation," PNAS USA 87(10):3758–3762 (1990).

Ross, R. et al., "A platelet–dependent serum factor that stimulates the proliferation of arterial smooth muscle cells in vitro," PNAS USA 71(4):1207–1210 (1974).

Shamblott, M.J. et al., "Derivation of pluripotent stem cells from cultured human primordial germ cells," PNAS USA 95(23):13726–13731 (1998).

Smith, A., "Cell therapy: in search of pluripotency," Curr. Biol. 8(22):R802–804 (1998).

Sirica, A.E. et al., "Use of primary cultures of adult rat hepatocytes on collagen gelnylon mesh to evaluate carcinogen–induced unscheduled DNA synthesis," Cancer Res. 40(9):3259–3265 (1980).

Sirica, A.E. et al., "Fetal phenotypic expression by adult rat hepatocytes on collagen gel/nylon meshes," PNAS USA 76(1):283–287 (1979).

Stein, I. et al., "Stabilization of vascular endothelial growth factor mRNA by hypoxia and hypoglycemia and corregulation with other ischemia–induced genes," Mol. Cell Biol. 15(10):5363–5368 (1995).

Thomson, J.A. et al., "Embryonic stem cell lines derived from human blastocysts," Science 282(5391):1145–1147 (1998).

Williams, J.T. et al., "Cells isolated from adult human skeletal muscle capable of differentiating into multiple mesodermal phenotypes," Am. Surg. 65(1):22–26 (1999).

Yang and De Bono, "A new role for vascular endothelial growth factor and fibroblast growth factors: increasing endothelial resistance to oxidative stress," FEBS Lett. 403(2):139–142 (1997).

Yao, D.L. et al., "Cryogenic spinal cord injury induces astrocytic gene expression of insulin–like growth factor 1 and insulin–like growth factor binding protein 2 during myelin regeneration," J. neurosci. Res. 40(5):647–659 (1995).

Oberley, T.D. et al., "Immunohistochemical Localization of Glutathione–S–transferase and Glutathione Peroxidase in Adult Syrian Hamster Tissues and During Kidney Development," Am J Pathology 139(2):355–369 (1991).

Wells–Knecht, M.C. et al., "Age–dependent Increase in Ortho–Tyrosine and Methionine Sulfoxide in Human Skin Collagen Is Not Accelerated in Diabetes," J. Clin. Investig 100(4):839–846 (1997).

WO00/069449 Search Report dated Nov. 29, 2000.

WO02/098365 Search Report dated Jan. 15, 2003.

EP02744248.2 Search Report dated Feb. 3, 2005.

* cited by examiner

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1, 21, 38 and 39 are cancelled.
Claims 2–20, 22–37 and 40–48 were not reexamined.
Other newly added claims 49–50 are canceled.

\* \* \* \* \*